(12) United States Patent
Prince et al.

(10) Patent No.: US 8,949,037 B2
(45) Date of Patent: Feb. 3, 2015

(54) METHOD AND SYSTEM FOR DETECTING AND MONITORING EMISSIONS

(75) Inventors: Dennis Scott Prince, Edmonton (CA); Terry Dan Butler, Edmonton (CA)

(73) Assignee: Airdar Inc., Edmonton (CA)

( * ) Notice: Subject to any disclaimer, the term of this patent is extended or adjusted under 35 U.S.C. 154(b) by 845 days.

(21) Appl. No.: 12/015,294

(22) Filed: Jan. 16, 2008

(65) Prior Publication Data

US 2008/0195329 A1    Aug. 14, 2008

Related U.S. Application Data

(63) Continuation-in-part of application No. 10/711,081, filed on Aug. 20, 2004, now Pat. No. 7,523,638.

(60) Provisional application No. 60/885,172, filed on Jan. 16, 2007, provisional application No. 60/481,266, filed on Aug. 20, 2003.

(51) Int. Cl.
  *G01N 27/00*    (2006.01)
  *G01N 33/00*    (2006.01)

(52) U.S. Cl.
  CPC ........ *G01N 33/0062* (2013.01); *G01N 33/0057* (2013.01)
  USPC ............................................. 702/23; 73/1.06

(58) Field of Classification Search
  USPC ................ 702/22–26, 30–32; 73/1.06, 23.31, 73/31.01, 31.02, 31.03, 31.06; 250/343
  See application file for complete search history.

(56) References Cited

U.S. PATENT DOCUMENTS

| | | | |
|---|---|---|---|
| 4,127,780 A | | 11/1978 | Kimbell |
| 4,135,092 A | * | 1/1979 | Milly .............................. 250/343 |
| 4,204,121 A | | 5/1980 | Milly |
| 5,099,437 A | | 3/1992 | Weber |
| 5,106,756 A | | 4/1992 | Zaromb |
| 5,386,373 A | | 1/1995 | Keeler |
| 5,604,299 A | * | 2/1997 | Cobb ............................ 73/31.02 |
| 5,719,396 A | | 2/1998 | Jack et al. |
| 5,726,450 A | | 3/1998 | Peterson et al. |
| 5,832,411 A | * | 11/1998 | Schatzmann et al. ........... 702/23 |
| 5,879,943 A | | 3/1999 | Ando et al. |
| 5,918,257 A | | 6/1999 | Mifsud et al. |
| 6,734,824 B2 | | 5/2004 | Herman |
| 6,895,335 B2 | | 5/2005 | Archibald |
| 2002/0169557 A1 | | 11/2002 | Gilbert et al. |
| 2005/0039515 A1 | | 2/2005 | Prince |

FOREIGN PATENT DOCUMENTS

JP    11118701 A    4/1999

OTHER PUBLICATIONS

The Alberta Oil Sands Community Exposure and Health Effects Assessment Program: Technical Report (Dr. Petros Koutrakis et al), Aug. 2000, pp. 206-217.

* cited by examiner

*Primary Examiner* — Manuel L Barbee
(74) *Attorney, Agent, or Firm* — Bennett Jones LLP

(57) ABSTRACT

A method and system for detecting, quantifying or characterizing emitting sources. According to an embodiment, an emission source is located by monitoring an area with one or more sensors, determining a plume, generating one or more candidates for the emission source, and using the plume to derive one or more characteristics associated with the emission source, and then locating the emission source based on agreement or convergence of the one or more characteristics.

6 Claims, 32 Drawing Sheets

| DATE | TIME | VALVE POSTION | THC PPM | WIND SPEED | WIND DIRECTION |
|---|---|---|---|---|---|
| 10/02/2006 | 4:58:59 PM | 1 | 5.684 | 14.136 | 207.611 |
| 10/02/2006 | 4:59:10 PM | 1 | 6.214 | 15.24 | 212.203 |
| 10/02/2006 | 4:59:21 PM | 1 | 5.352 | 15.251 | 210.611 |
| 10/02/2006 | 4:59:32 PM | 1 | 4.767 | 14.148 | 205.116 |
| 10/02/2006 | 4:59:43 PM | 1 | 4.674 | 14.598 | 201.061 |
| 10/02/2006 | 4:59:54 PM | 1 | 4.332 | 16.067 | 203.956 |
| 10/02/2006 | 5:00:04 PM | 1 | 5.189 | 16.168 | 207.08 |
| 10/02/2006 | 5:00:15 PM | 1 | 4.757 | 17.204 | 205.982 |
| 10/02/2006 | 5:00:26 PM | 1 | 4.118 | 13.129 | 204.381 |
| 10/02/2006 | 5:00:37 PM | 2 | 5.685 | 12.23 | 199.198 |
| 10/02/2006 | 5:00:47 PM | 2 | 5.438 | 13.729 | 193.871 |
| 10/02/2006 | 5:00:58 PM | 2 | 4.579 | 14.784 | 195.407 |
| 10/02/2006 | 5:01:09 PM | 2 | 5.176 | 14.606 | 206.973 |
| 10/02/2006 | 5:01:20 PM | 2 | 5.322 | 14.684 | 200.247 |
| 10/02/2006 | 5:01:30 PM | 2 | 5.54 | 16.767 | 208.745 |
| 10/02/2006 | 5:01:41 PM | 2 | 5.523 | 13.655 | 212.037 |
| 10/02/2006 | 5:01:52 PM | 2 | 5.538 | 16.657 | 205.234 |
| 10/02/2006 | 5:02:03 PM | 2 | 5.227 | 16.107 | 203.824 |
| 10/02/2006 | 5:02:14 PM | 2 | 5.247 | 15.817 | 204.575 |
| 10/02/2006 | 5:02:25 PM | 2 | 5.271 | 15.766 | 205.533 |
| 10/02/2006 | 5:02:35 PM | 2 | 5.434 | 15.175 | 206.567 |
| 10/02/2006 | 5:02:46 PM | 2 | 5.603 | 14.77 | 204.074 |
| 10/02/2006 | 5:02:57 PM | 2 | 5.936 | 11.35 | 189.12 |
| 10/02/2006 | 5:03:08 PM | 2 | 6.31 | 13.183 | 204.772 |
| 10/02/2006 | 5:03:19 PM | 2 | 6.116 | 14.372 | 202.819 |
| 10/02/2006 | 5:03:30 PM | 2 | 5.368 | 13.133 | 206.831 |
| 10/02/2006 | 5:03:40 PM | 4 | 5.432 | 11.733 | 196.167 |
| 10/02/2006 | 5:03:51 PM | 4 | 5.389 | 15.439 | 200.088 |
| 10/02/2006 | 5:04:02 PM | 4 | 4.155 | 16.015 | 211.529 |
| 10/02/2006 | 5:04:13 PM | 4 | 3.474 | 12.914 | 200.656 |
| 10/02/2006 | 5:04:24 PM | 4 | 3.557 | 12.981 | 194.141 |
| 10/02/2006 | 5:04:35 PM | 4 | 3.346 | 12.064 | 200.449 |
| 10/02/2006 | 5:04:45 PM | 4 | 3.232 | 14.116 | 206.768 |
| 10/02/2006 | 5:04:56 PM | 4 | 3.293 | 15.537 | 206.267 |
| 10/02/2006 | 5:05:07 PM | 4 | 3.237 | 15.303 | 198.882 |
| 10/02/2006 | 5:05:18 PM | 4 | 3.399 | 14.075 | 210.995 |
| 10/02/2006 | 5:05:29 PM | 4 | 3.295 | 12.34 | 193.558 |
| 10/02/2006 | 5:05:40 PM | 4 | 3.311 | 12.455 | 198.452 |
| 10/02/2006 | 5:05:50 PM | 4 | 3.556 | 12.472 | 194.59 |
| 10/02/2006 | 5:06:01 PM | 4 | 3.368 | 13.516 | 195.11 |
| 10/02/2006 | 5:06:12 PM | 4 | 3.352 | 16.963 | 200.493 |

FIG. 4

| DATE | TIME | LATITUDE | LONGITUDE |
|---|---|---|---|
| 11/10/2006 | 04:00:36 | 53.214373 | 113.234838 |
| 11/10/2006 | 04:00:46 | 53.214373 | 113.234838 |
| 11/10/2006 | 04:00:56 | 53.214373 | 113.234838 |
| 11/10/2006 | 04:01:06 | 53.214373 | 113.234838 |
| 11/10/2006 | 04:01:16 | 53.214373 | 113.234838 |
| 11/10/2006 | 04:01:26 | 53.214373 | 113.234838 |
| 11/10/2006 | 04:01:37 | 53.214373 | 113.234838 |
| 11/10/2006 | 04:01:47 | 53.214373 | 113.234838 |
| 11/10/2006 | 04:01:57 | 53.214373 | 113.234838 |
| 11/10/2006 | 04:02:07 | 53.214373 | 113.234838 |
| 11/10/2006 | 04:02:17 | 53.214373 | 113.234838 |
| 11/10/2006 | 04:02:27 | 53.214373 | 113.234838 |
| 11/10/2006 | 04:02:38 | 53.214373 | 113.234838 |
| 11/10/2006 | 04:02:48 | 53.214373 | 113.234838 |
| 11/10/2006 | 04:02:58 | 53.214373 | 113.234838 |
| 11/10/2006 | 04:03:08 | 53.214373 | 113.234838 |
| 11/10/2006 | 04:03:18 | 53.213957 | 113.235293 |
| 11/10/2006 | 04:03:28 | 53.213957 | 113.235293 |
| 11/10/2006 | 04:03:39 | 53.213957 | 113.235293 |
| 11/10/2006 | 04:03:49 | 53.213957 | 113.235293 |
| 11/10/2006 | 04:03:59 | 53.213957 | 113.235293 |
| 11/10/2006 | 04:04:09 | 53.213957 | 113.235293 |
| 11/10/2006 | 04:04:19 | 53.213957 | 113.235293 |
| 11/10/2006 | 04:04:29 | 53.213957 | 113.235293 |
| 11/10/2006 | 04:04:40 | 53.213957 | 113.235293 |
| 11/10/2006 | 04:04:50 | 53.213957 | 113.235293 |
| 11/10/2006 | 04:05:00 | 53.213957 | 113.235293 |
| 11/10/2006 | 04:05:10 | 53.213957 | 113.235293 |

FIG. 5a

| ELEVATION | VALVE POSITION | THC | WIND SPEED | WIND DIRECTION | FLOW 1 | FLOW 2 |
|---|---|---|---|---|---|---|
| 1050 | 1 | 1.63 | 3.39 | 57.04 | 0.69 | 1.28 |
| 1050 | 1 | 1.6 | 2.66 | 59.09 | 0.71 | 1.28 |
| 1050 | 1 | 1.59 | 3.02 | 55.52 | 0.73 | 1.28 |
| 1050 | 1 | 1.56 | 4.53 | 41.36 | 0.74 | 1.28 |
| 1050 | 1 | 1.56 | 5.11 | 38.02 | 0.75 | 1.28 |
| 1050 | 1 | 1.54 | 5.64 | 35.98 | 0.75 | 1.28 |
| 1050 | 1 | 1.54 | 6.51 | 35.65 | 0.76 | 1.28 |
| 1050 | 1 | 1.53 | 6.56 | 40.67 | 0.76 | 1.28 |
| 1050 | 1 | 1.52 | 7.21 | 37.04 | 0.77 | 1.28 |
| 1050 | 1 | 1.54 | 7.19 | 35.84 | 0.77 | 1.28 |
| 1050 | 1 | 1.55 | 7.43 | 35.47 | 0.77 | 1.28 |
| 1050 | 1 | 1.54 | 8.55 | 36.94 | 0.77 | 1.28 |
| 1050 | 1 | 1.52 | 7.64 | 44.13 | 0.77 | 1.28 |
| 1050 | 1 | 1.52 | 8.07 | 39.09 | 0.77 | 1.28 |
| 1050 | 1 | 1.54 | 7.12 | 35.14 | 0.77 | 1.28 |
| 1050 | 1 | 1.54 | 9.78 | 28.04 | 0.77 | 1.28 |
| 1080 | 3 | 1.54 | 10.3 | 29.52 | 1.06 | 1.13 |
| 1080 | 3 | 1.55 | 9.34 | 29.13 | 1.11 | 1.08 |
| 1080 | 3 | 1.27 | 8.95 | 29.21 | 1.05 | 1.08 |
| 1080 | 3 | 1.29 | 8.09 | 29.78 | 1.02 | 1.08 |
| 1080 | 3 | 1.27 | 7.84 | 32 | 1 | 1.08 |
| 1080 | 3 | 1.29 | 7.93 | 31.07 | 0.98 | 1.08 |
| 1080 | 3 | 1.28 | 7.77 | 35.5 | 0.97 | 1.08 |
| 1080 | 3 | 1.42 | 9.68 | 31.59 | 0.96 | 1.08 |
| 1080 | 3 | 1.39 | 9.13 | 31.57 | 0.95 | 1.08 |
| 1080 | 3 | 1.3 | 9.59 | 31.03 | 0.95 | 1.08 |
| 1080 | 3 | 1.28 | 8.58 | 30.55 | 0.95 | 1.08 |
| 1080 | 3 | 1.34 | 8.95 | 30.25 | 0.94 | 1.08 |

FIG. 5b

| FLOW 3 | FLOW 4 | FLOW 5 | FLOW 6 | FLOW 7 | FLOW 8 |
|---|---|---|---|---|---|
| 1.25 | 1.48 | 1.09 | 1.48 | 0.94 | 1.36 |
| 1.25 | 1.48 | 1.09 | 1.48 | 0.96 | 1.36 |
| 1.25 | 1.48 | 1.09 | 1.48 | 0.98 | 1.36 |
| 1.25 | 1.48 | 1.09 | 1.48 | 0.98 | 1.36 |
| 1.25 | 1.48 | 1.09 | 1.48 | 0.98 | 1.36 |
| 1.25 | 1.48 | 1.09 | 1.48 | 0.99 | 1.36 |
| 1.25 | 1.48 | 1.09 | 1.47 | 0.99 | 1.36 |
| 1.25 | 1.48 | 1.09 | 1.48 | 0.99 | 1.36 |
| 1.25 | 1.48 | 1.09 | 1.48 | 0.99 | 1.36 |
| 1.25 | 1.48 | 1.09 | 1.48 | 0.99 | 1.36 |
| 1.25 | 1.48 | 1.09 | 1.48 | 0.99 | 1.36 |
| 1.25 | 1.48 | 1.09 | 1.48 | 0.99 | 1.36 |
| 1.25 | 1.48 | 1.09 | 1.48 | 0.99 | 1.36 |
| 1.25 | 1.48 | 1.09 | 1.48 | 0.99 | 1.36 |
| 1.25 | 1.48 | 1.09 | 1.48 | 0.99 | 1.36 |
| 1.25 | 1.48 | 1.09 | 1.48 | 0.99 | 1.36 |
| 1.25 | 1.47 | 1.09 | 1.46 | 0.97 | 1.34 |
| 1.27 | 1.5 | 1.1 | 1.49 | 1 | 1.37 |
| 1.27 | 1.5 | 1.1 | 1.49 | 1.01 | 1.37 |
| 1.27 | 1.5 | 1.11 | 1.49 | 1.01 | 1.38 |
| 1.27 | 1.51 | 1.11 | 1.5 | 1.01 | 1.38 |
| 1.27 | 1.51 | 1.11 | 1.5 | 1.01 | 1.38 |
| 1.27 | 1.51 | 1.11 | 1.5 | 1.01 | 1.38 |
| 1.27 | 1.51 | 1.11 | 1.5 | 1.01 | 1.38 |
| 1.27 | 1.51 | 1.11 | 1.5 | 1.01 | 1.38 |
| 1.27 | 1.51 | 1.11 | 1.5 | 1.01 | 1.38 |
| 1.27 | 1.51 | 1.11 | 1.5 | 1.01 | 1.38 |
| 1.27 | 1.51 | 1.11 | 1.5 | 1.01 | 1.38 |

FIG. 5c

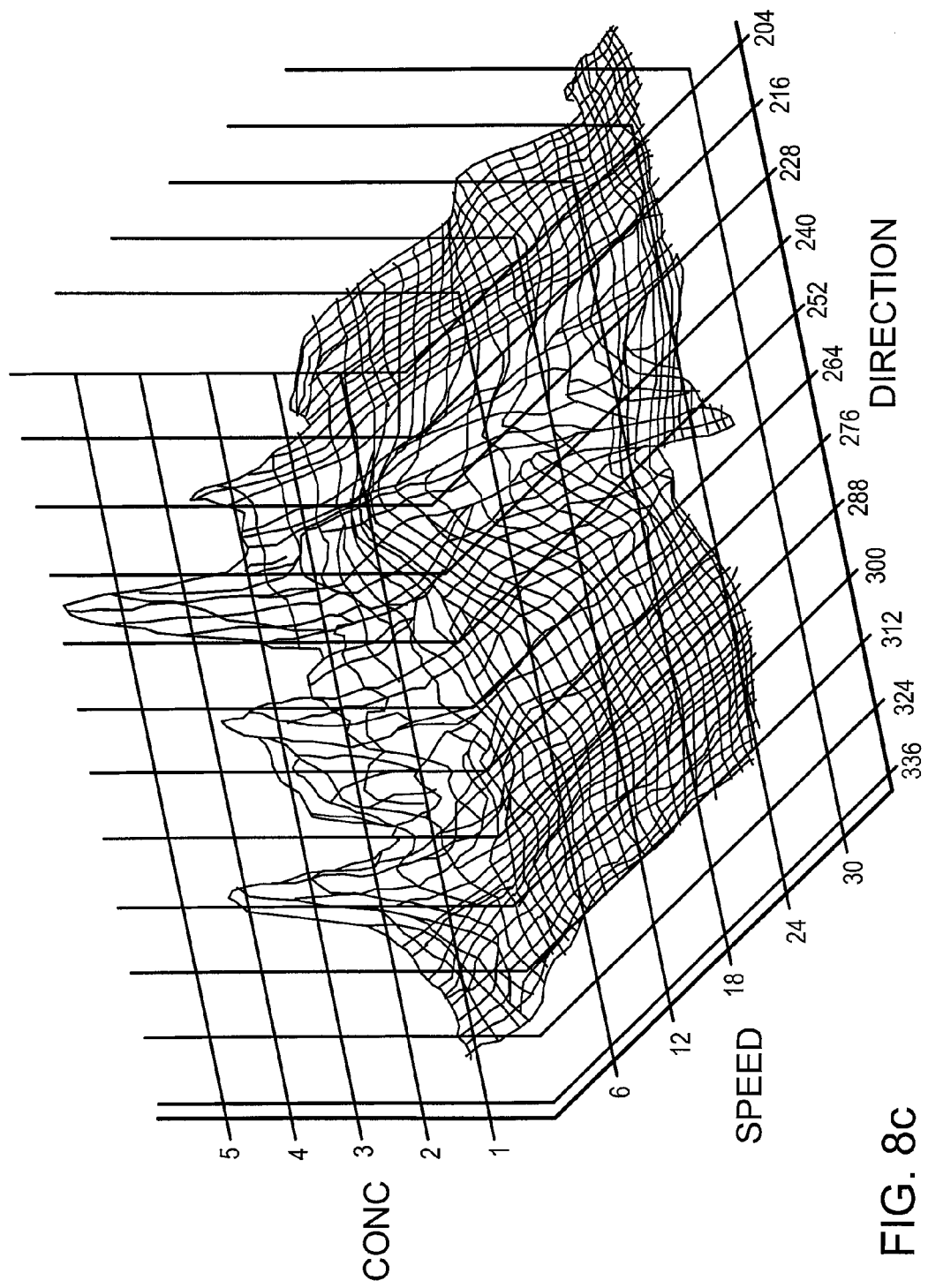

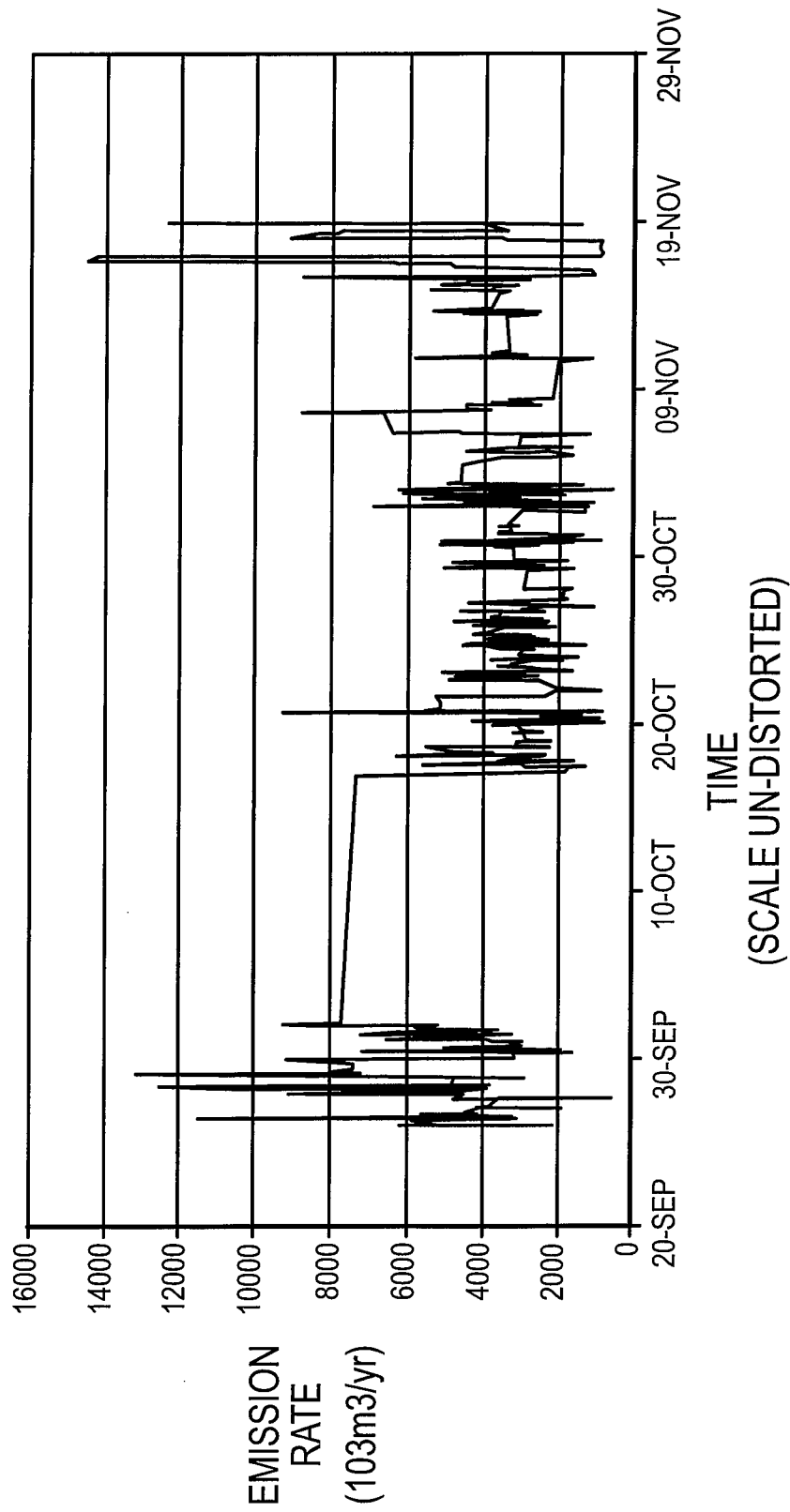

METHOD AND SYSTEM FOR DETECTING AND MONITORING EMISSIONS

FIELD OF THE INVENTION

The present invention relates to air monitoring, and in particular to a method and system for detecting, quantifying or characterizing emitting sources.

BACKGROUND OF THE INVENTION

The reduction of industrial contaminant emissions continues to be important in decreasing anthropogenic environmental impact. Daunting challenges are being encountered as the bar continues to rise with respect to both the amount and nature of contaminants that are considered acceptable. This is particularly evident with respect to Green House Gas (GHG) emission reductions. While large $CO_2$ emissions are a present concern with respect to the green house effect, unintended emissions of methane would also be important given that methane produces a greater green house effect. The contribution of methane emissions to the overall anthropogenic environmental impact is not presently well understood, however there are indications that it may be significant.

In the field of air quality monitoring, human sensory perception is relied upon to detect chemical or particulate plumes. Visible plumes may also include condensation plumes, wherein an emitted contaminant being otherwise invisible, becomes visible under atmospheric temperature and pressure conditions causing the contaminant to condensate or crystallize. If a plume has distinctive visual characteristics, such as a distinctive color or opaqueness, the plume can be tracked visually back to its source. However, human visual sensory perception cannot be relied upon in low lighting conditions.

Not all emissions have discernable visual characteristics. Whether an emission does not have discernable visual characteristics under typical environmental conditions, whether an emission has discernable visual characteristics however it is of such low concentration that human sensory perception is incapable of perceiving the difference between the plume and the ambient air, or whether smoggy environmental conditions render the plume indistinguishable therefrom; even extremely low concentrations of certain airborne contaminants can have a deleterious impact on the environment and/or affect living entities large and small.

Accordingly, there remains a need for improvements in the art.

BRIEF SUMMARY OF THE INVENTION

The present invention is directed to a method and system for detecting, quantifying and/or characterizing sources of an emission of a material or compound.

In accordance with a broad aspect of the present invention, there is provided a method of characterizing a source of an emitted material, the method comprises the steps of: measuring concentrations of the emitted material from at least two or more locations; measuring changes in representative wind velocity over time; generating a first dimensionless plume and a second dimensionless plume in space based on the measured wind velocity changes and the measured concentrations at the first and the second locations, respectively; determining a first trajectory based on the measured wind velocity changes and the measured concentrations for the first location; determining a second trajectory based on the measured wind velocity changes and the measured concentrations for the second location; determining a first emission source candidate at a first location along the first trajectory, and the first emission source having one or more characteristics; determining a second emission source candidate at a second location along the second trajectory, and the second emission source having one or more characteristics; converting the first dimensionless plume into a dimensioned plume at the first location and determining a size characteristic based on said dimensioned plume, wherein the size characteristic comprises one of the characteristics associated with the first emission source candidate; converting the second dimensionless plume into a dimensioned plume at the second location and determining a size characteristic associated with the second source candidate based on the dimensioned plume, wherein the size characteristic comprises one of the characteristics associated with the second emission source candidate; and determining the source of the emitted material based on substantial agreement between the location and the characteristics of the first and second emission source candidates.

In accordance with another broad aspect of the present invention, there is provided a method of characterizing a source of an emitted material, the method comprises the steps of: measuring concentrations of the emitted material from at least one location; measuring changes in wind velocity over time; generating a dimensionless plume in space based on the measured concentrations and the measured wind velocity changes; determining a trajectory for the dimensionless plume; determining one or more characteristics associated with the dimensionless plume; determining one or more emission source candidates at locations along the trajectory, wherein each of the candidates includes one or more characteristics; converting the dimensionless plume into a dimensioned plume at the location of each of the candidates, and determining a characteristic associated with each of the emission source candidates based on the corresponding dimensioned plume; obtaining a characteristic associated with the source of the emission; and determining the source of the emitted material based on substantial agreement between the location of one of the emission source candidates and the characteristic of the emission source.

According to another embodiment, there is provided a computer readable medium configured to store computer readable instructions executable by a computing device to cause the device to implement one or more of the processes and method described herein.

In accordance with a further aspect of the present invention, there is provided a method of characterizing a source emitting a contaminant into a moving fluid, the contaminant forming a plume, the method comprising the steps of: measuring a variation of a diluted concentration of the contaminant perceived at one or more sampling inlet locations about the source, the diluted contaminant concentration varying over time with a corresponding representative wind velocity; deriving a variation of a diluted contaminant flux per unit plume footprint cross-sectional area with the representative wind velocity at each sample inlet location as a function of the representative wind velocity; deriving an emission rate of a candidate contaminant emission source corresponding to each sampling inlet location based on the corresponding variation of the diluted contaminant flux per unit area, each candidate source being presumed to be located at a parcel of land located about the sampling inlet locations; comparing emission rate values of a first group of candidate sources; and asserting that the contaminant emission source is located at the parcel of land based on a substantial agreement between a subgroup of candidate source emission rates of the first group of candidate sources.

In accordance with another aspect of the present invention, there is provided a method for deriving the variation of the diluted contaminant flux per unit area comprises multiplying each diluted concentration measurement with the corresponding representative wind velocity determined based on weighted contributions of a plurality of wind velocity measurements measured prior to the diluted concentration measurement.

In accordance with a further aspect of the present invention, there is provided a method for deriving the emission rate of each candidate source comprising, for each sample inlet location identifying a predominant peaked flux distribution along the directional component of the wind velocity of the variation of diluted contaminant flux per unit area; for each sample inlet location characterizing the predominant peaked flux distribution with respect to a peak flux magnitude, a prevailing direction and a peak azimuthal width; selecting the parcel of land to have a location defined by the locus of intersections of vectors emanating from each sample inlet location along the corresponding prevailing directions; and multiplying the peak flux magnitude and a plume cross-sectional area at the sample inlet.

In accordance with a further aspect of the present invention, the method further comprises: determining a relative concentration for each concentration measurement at the representative wind velocity with respect to the average variation of the diluted contaminant concentration at the representative wind velocity; and asserting a corresponding relative emission rate deviation from an average emission rate at the representative wind velocity at a previous time corresponding to the plurality of wind velocity measurements and a measurement sampling rate.

In accordance with a further aspect of the present invention, the method further comprises: deriving an average variation of the diluted concentration of the contaminant with representative wind velocity determined for at least one of the sampling inlet locations; determining a relative concentration of each concentration measurement at the representative wind velocity with respect to the average variation of the diluted contaminant concentration at the representative wind velocity; and asserting a corresponding relative emission rate change of the contaminant source emission rate from an average contaminant source emission rate at a previous time corresponding to distance between the contaminant emission source location and the sampling inlet location divided by a speed component of the corresponding representative wind velocity.

In accordance with another aspect of the present invention, there is provided a method of locating at least two sources emitting a contaminant into a moving fluid, the contaminant forming one or more plumes, the method comprising: measuring a variation of a diluted concentration of the contaminant at least two sampling inlet locations about the sources, the diluted contaminant concentration varying over time with a corresponding representative wind velocity; determining a flux with the representative wind velocity at each sample inlet location as a function of the representative wind velocity; for each sample inlet location, identifying any peaked flux distributions along the directional component of the wind velocity of the variation of the flux; characterizing each peaked flux distribution of each sample inlet location with respect to a prevailing direction; for each peaked flux distribution defining a directional vector passing through from the corresponding sampling inlet location in the corresponding prevailing direction; selecting a group of vectors having a vector corresponding to each sample inlet location; and performing a method of characterizing a contaminant source using the peaked flux distributions corresponding to a subgroup of vectors.

In accordance with a broad aspect of the present invention, there is provided a method of monitoring a contaminant emission from at least one source, the method comprising: measuring a variation of a diluted concentration of the contaminant perceived at a sampling inlet location, the diluted contaminant concentration varying over time with a corresponding representative wind velocity; determining a variation of a diluted contaminant flux per unit contaminant plume footprint cross-sectional area with the representative wind velocity at the sample inlet location as a function of the representative wind velocity; determining an emission rate corresponding to the sampling inlet location by multiplying an average diluted contaminant flux per unit area within a predefined azimuthal width centered about a direction pointing to a locus of the at least one emission source and an emission plume cross-sectional area at the sample inlet location.

It is to be understood that other aspects of the present invention will become readily apparent to those skilled in the art from the following detailed description, wherein various embodiments of the invention are shown and described by way of illustration. As will be realized, the invention is capable for other and different embodiments and its several details are capable of modification in various other respects, all without departing from the spirit and scope of the present invention. Accordingly the drawings and detailed description are to be regarded as illustrative in nature and not as restrictive.

BRIEF DESCRIPTION OF THE DRAWINGS

Referring to the drawings wherein like reference numerals indicate similar parts throughout the several views, several aspects of the present invention are illustrated by way of example, and not by way of limitation, in the drawings, wherein:

FIG. 4 shows tabulated air sample analysis measurements recorded using a stationary setup;

FIG. 5a, FIG. 5b, and FIG. 5c show tabulated air sample analysis measurements recorded using a mobile setup;

FIG. 8a, FIG. 8b, and FIG. 8c show different perspectives of a variation of a contaminant concentration measurements varying with wind speed and direction shown in FIG. 7;

FIG.

Figure 11:
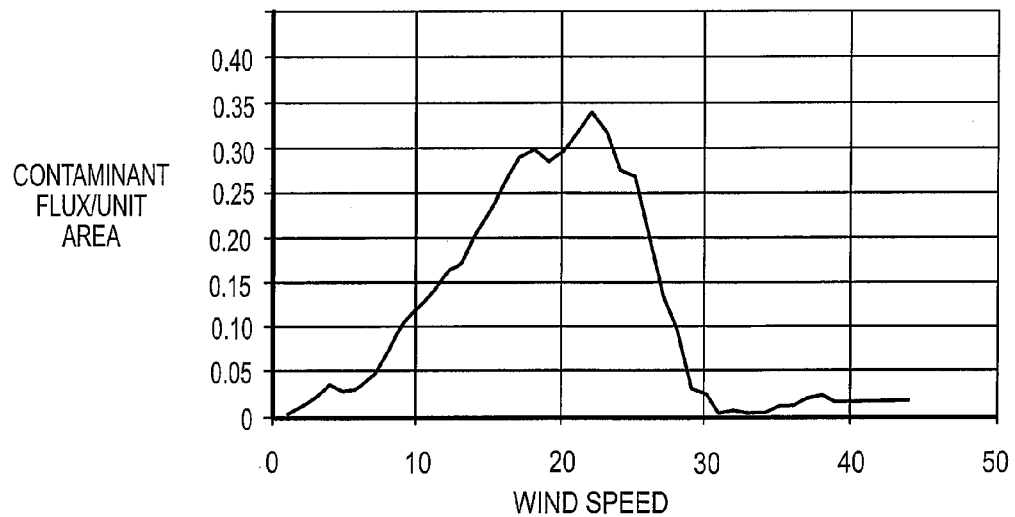
Figure 12:
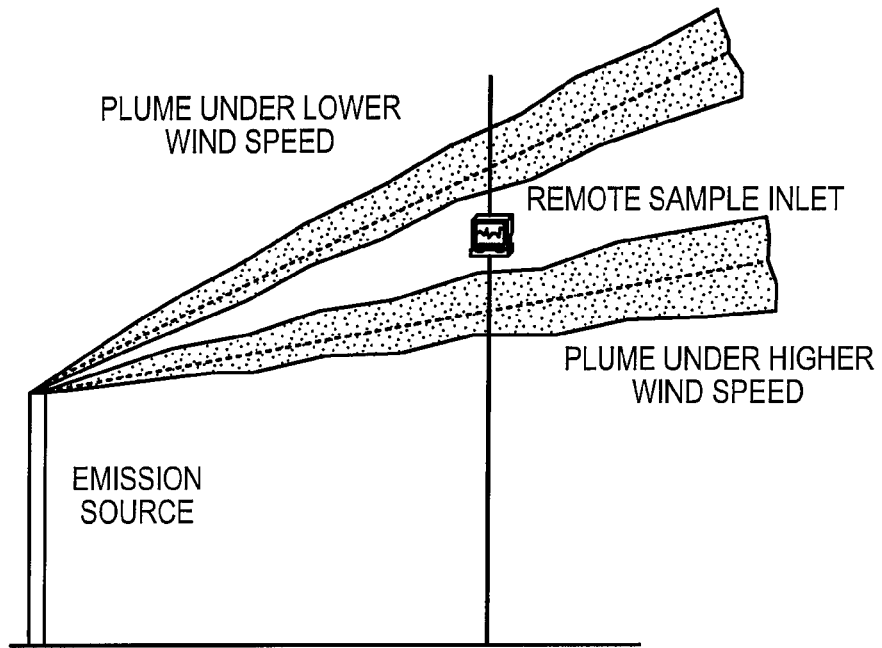
Figure 13:
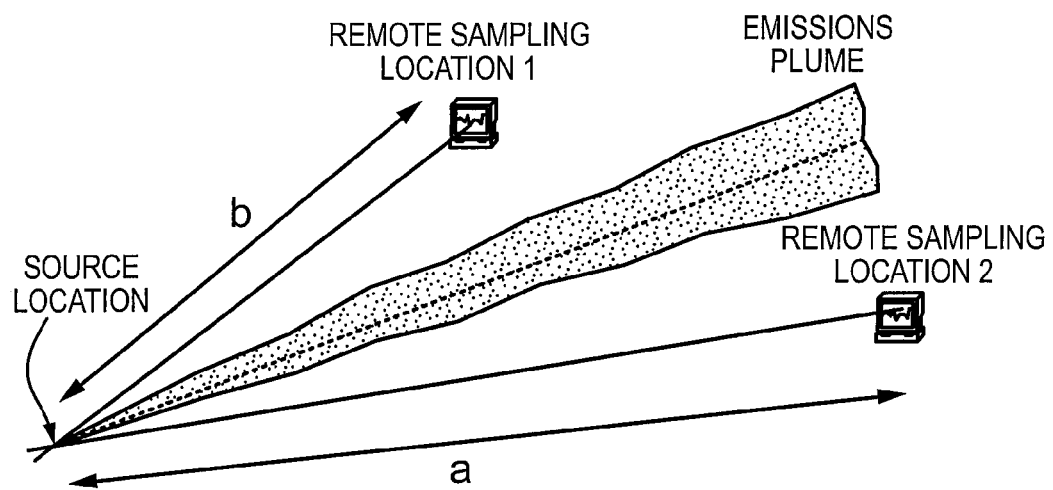
Figure 14:
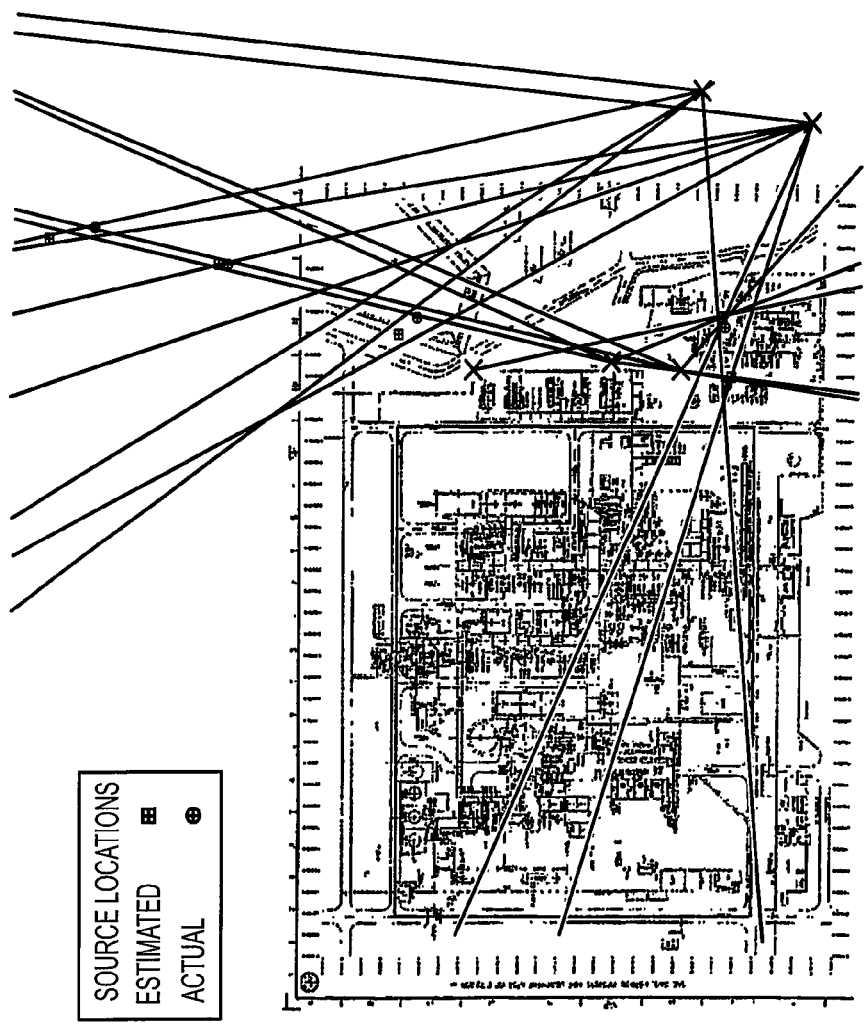
Figure 15:
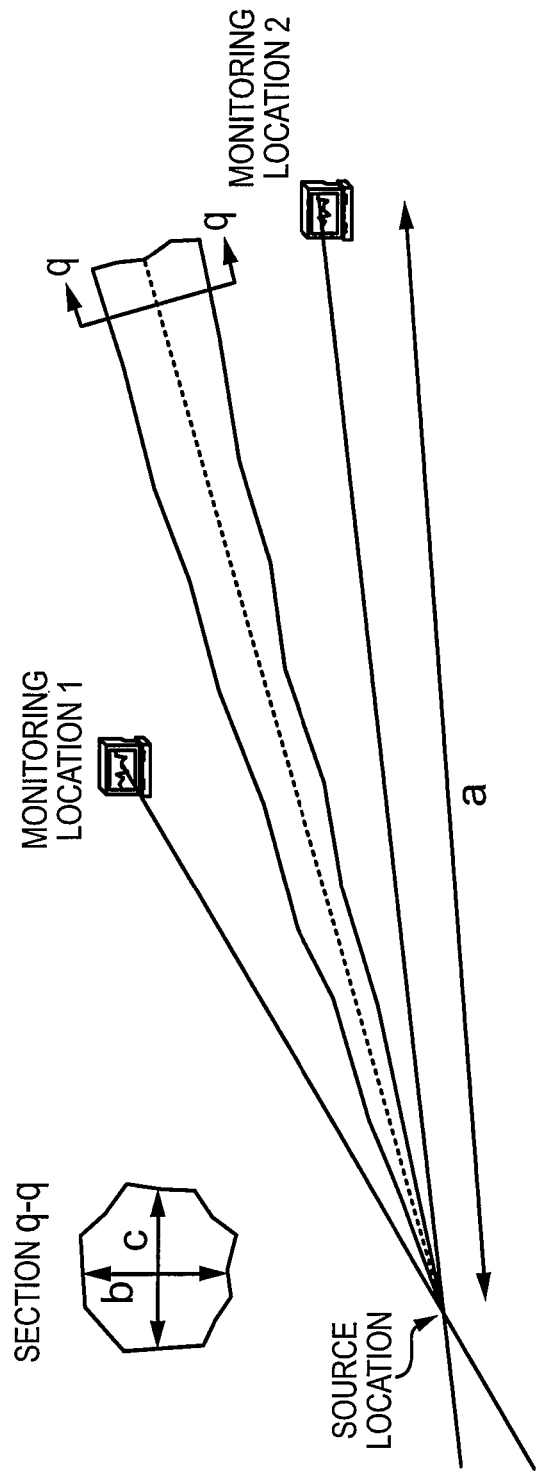
Figure 16:
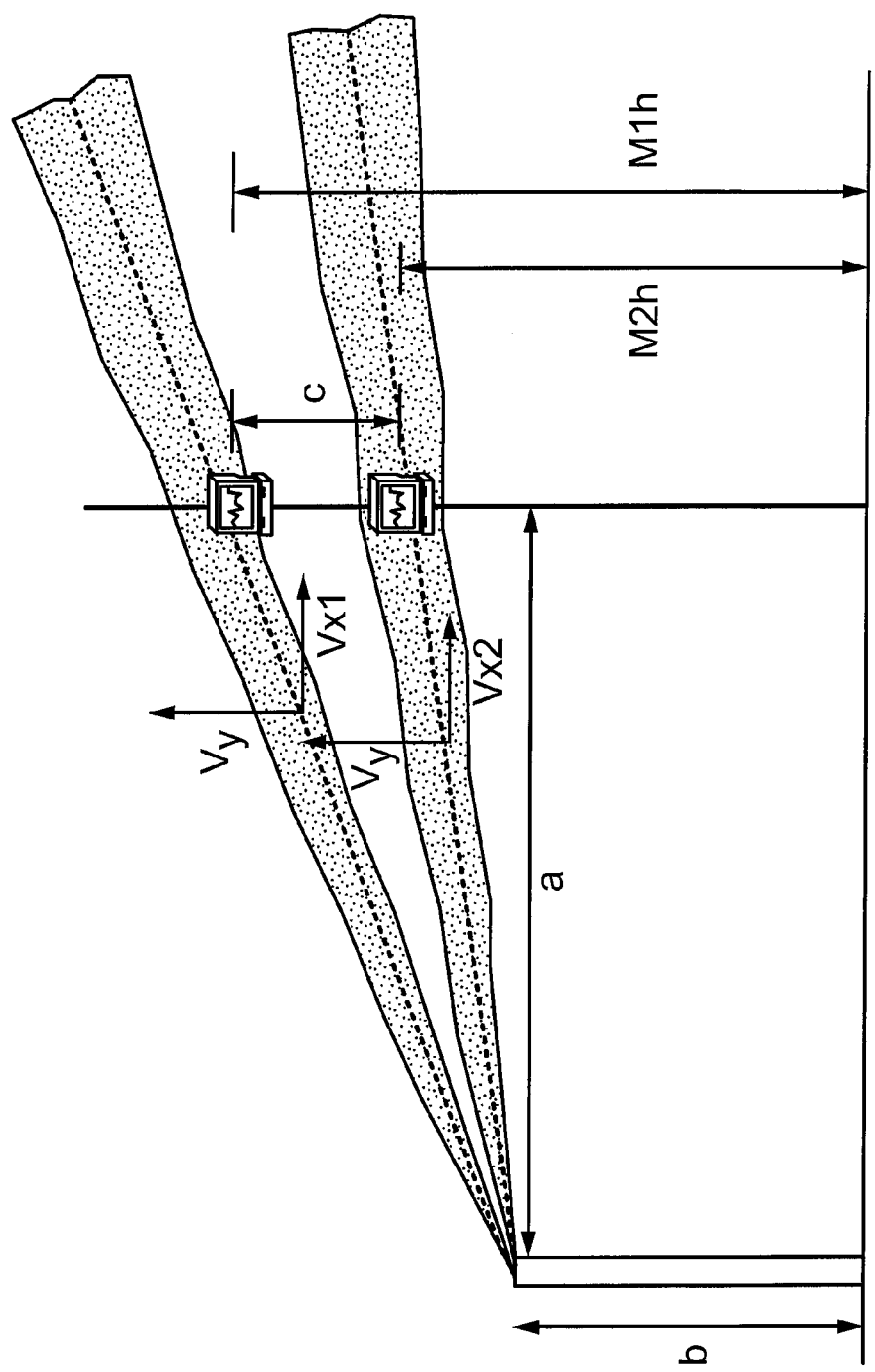
Figure 17:
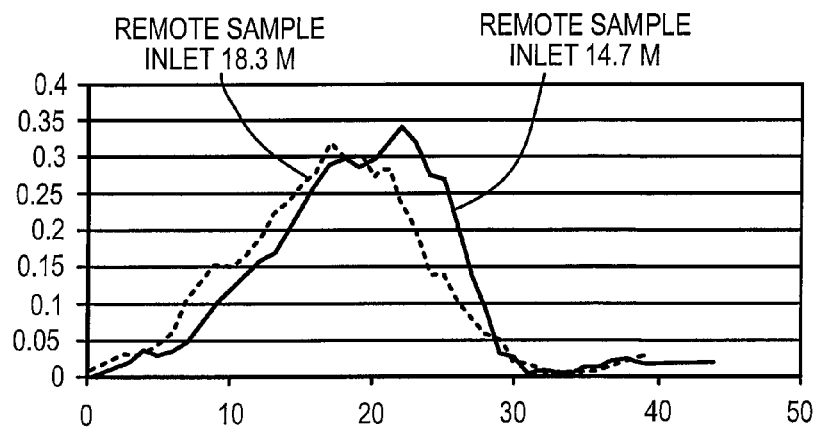
Figure 19:
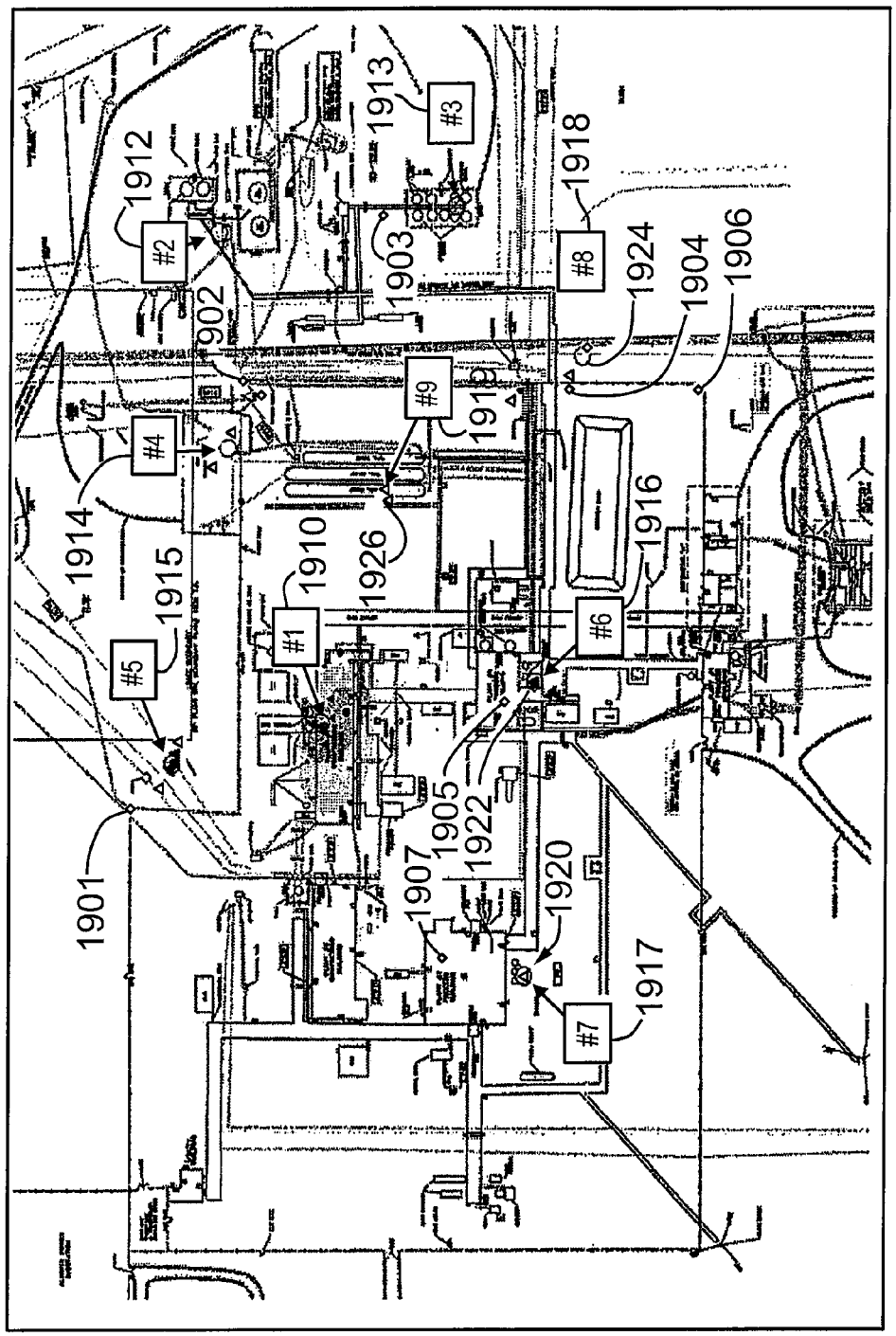
Figure 20:
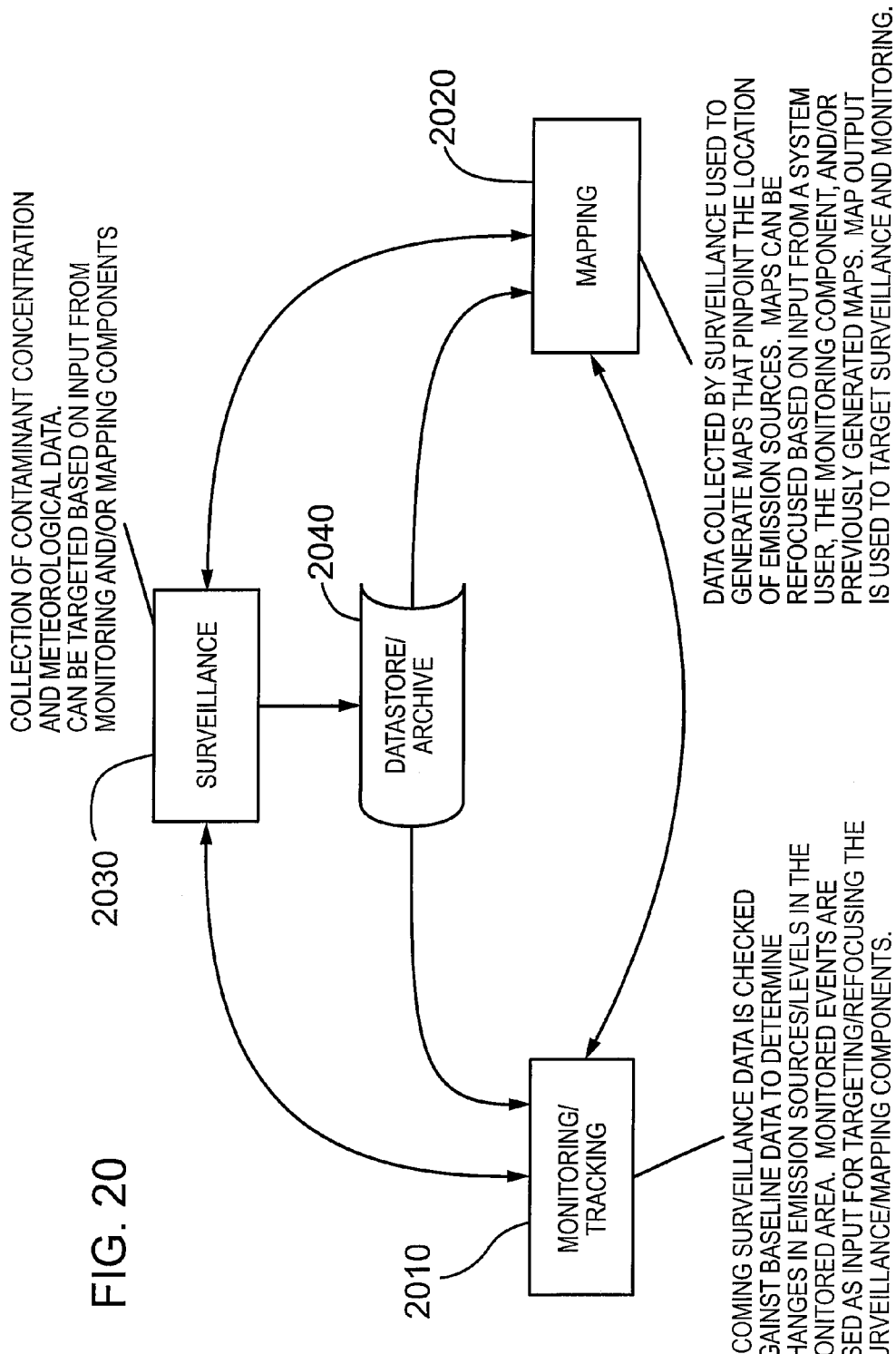
Figure 21:
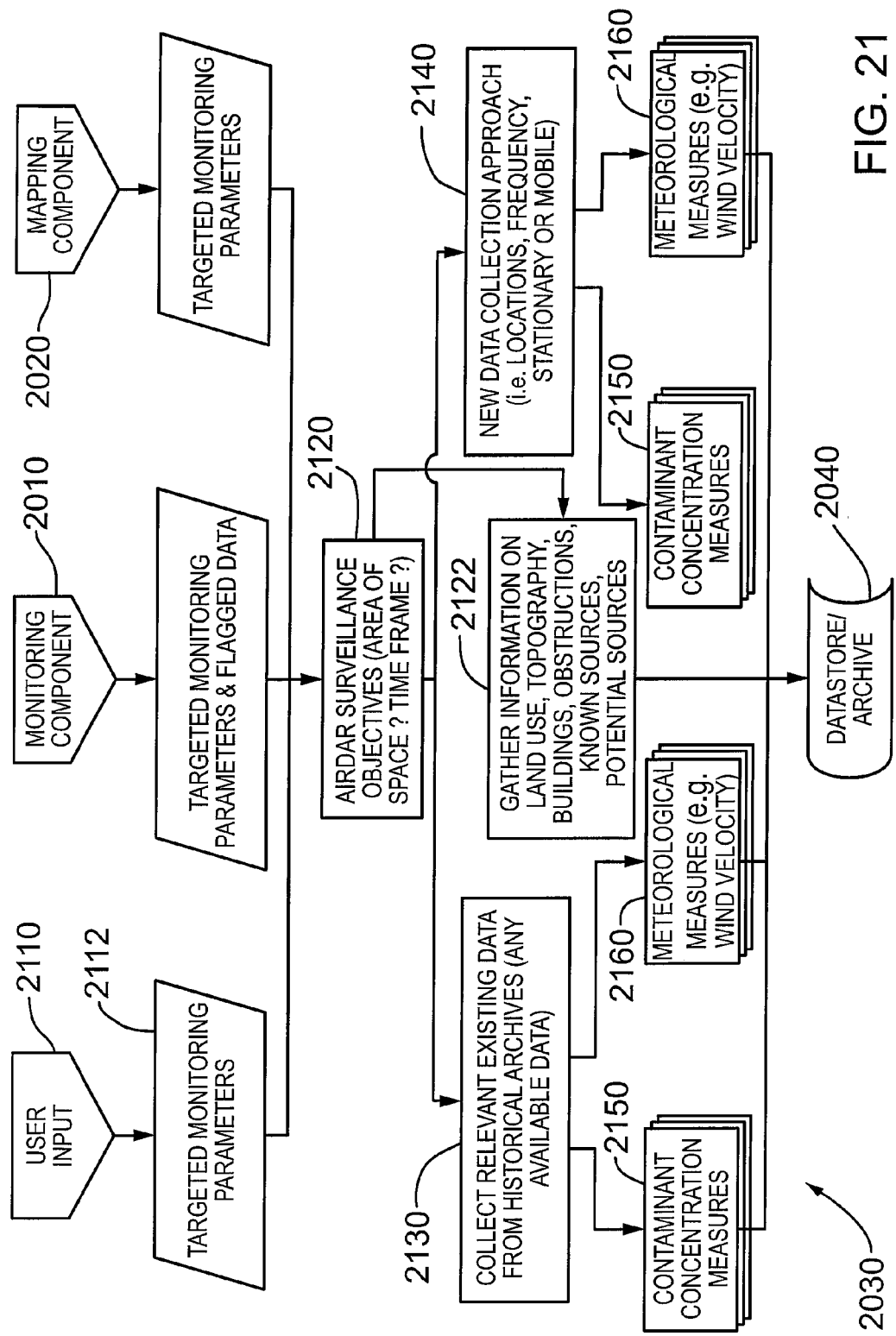

FIG. 11 is a graph showing contaminant flux varying with wind speed;

FIG. 12 is a schematic representation of the shifting of a plume with wind speed;

FIG. 13 is a schematic representation of emitting source location prediction by triangulation;

FIG. 14 is an example of an actual plot of predicted emitting sources by triangulation;

FIG. 15 is a schematic representation of relevant variables employed in quantifying the size of the leak;

FIG. 16 is a schematic representation of relevant variables employed in determining the height of a contamination emission source;

FIG. 17 shows two variations of flux per unit area versus wind velocity taken from two remote sampling inlets at the same location but at different elevations;

FIGS. 18a to 18d show exemplary graphs of contaminant emission variability for a contamination emission source with time;

FIG. 19 shows a map of a physical area with emission sources detected in accordance with an embodiment of the present invention;

FIG. 20 is a flowchart of a process according to an embodiment of the present invention;

FIG. 21 is a flowchart of a process for performing surveillance and gathering potentially relevant data for determining emission sources according to an embodiment of the present invention.

Figure 22:
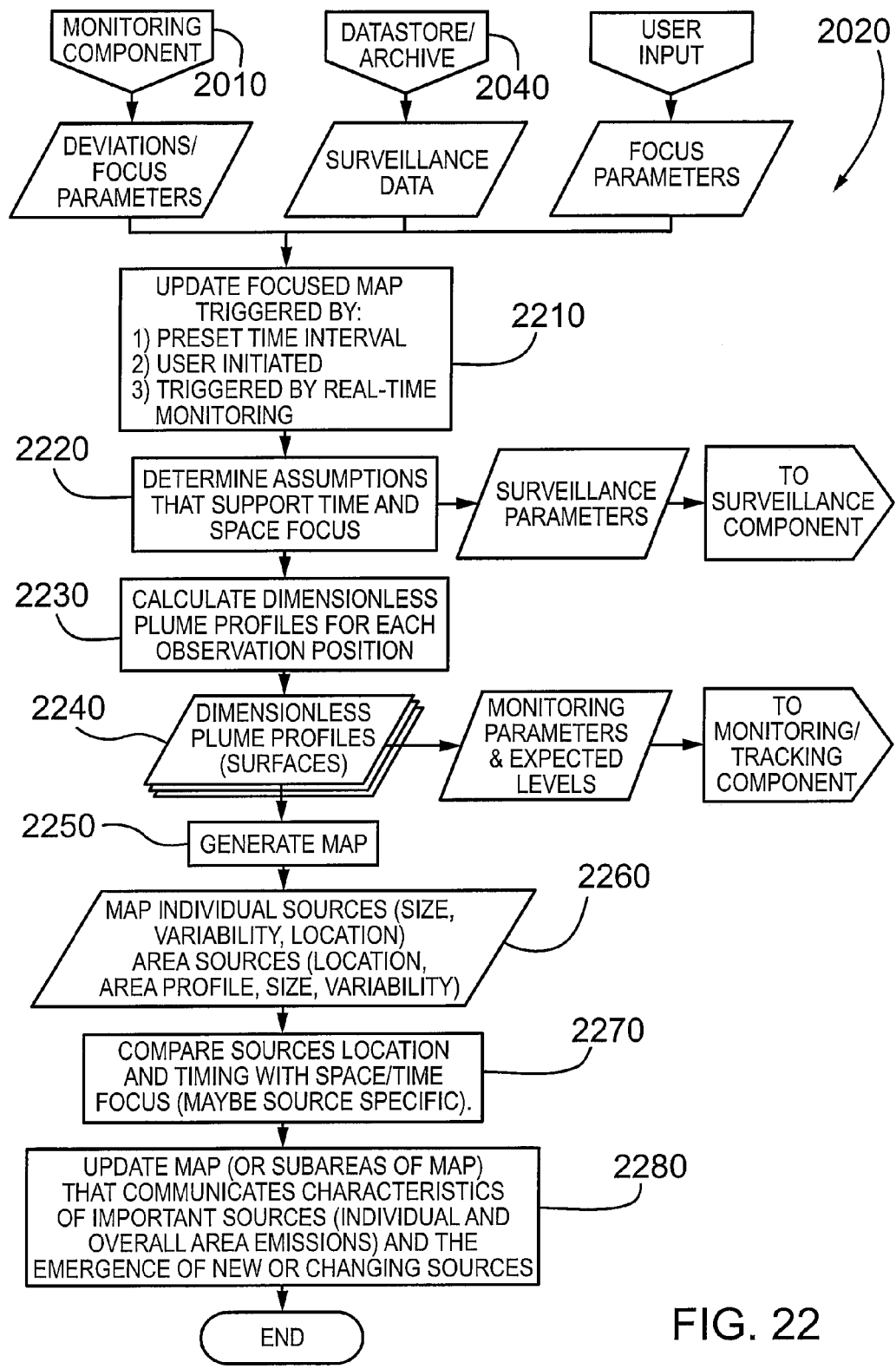
Figure 23A:
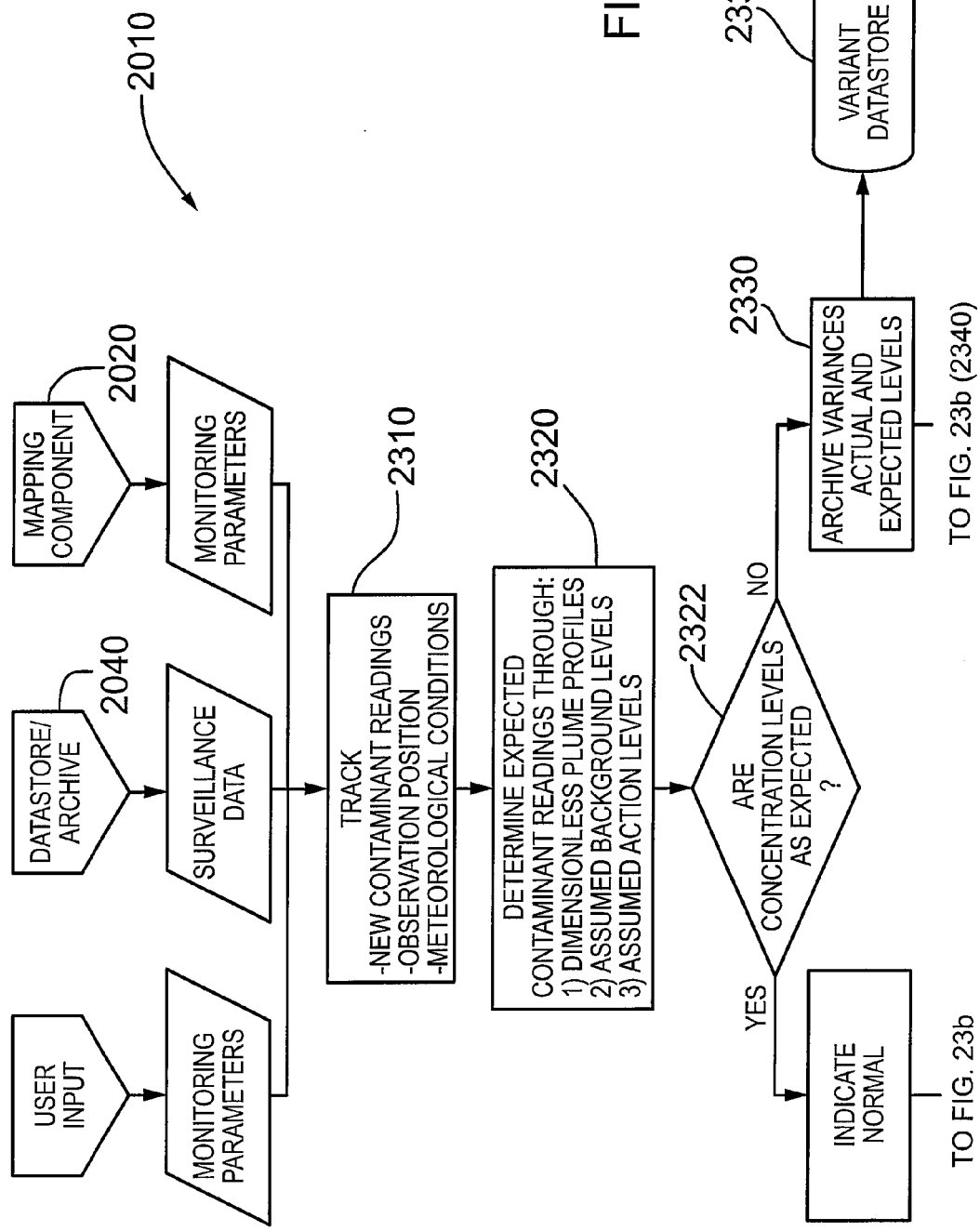
Figure 23B:
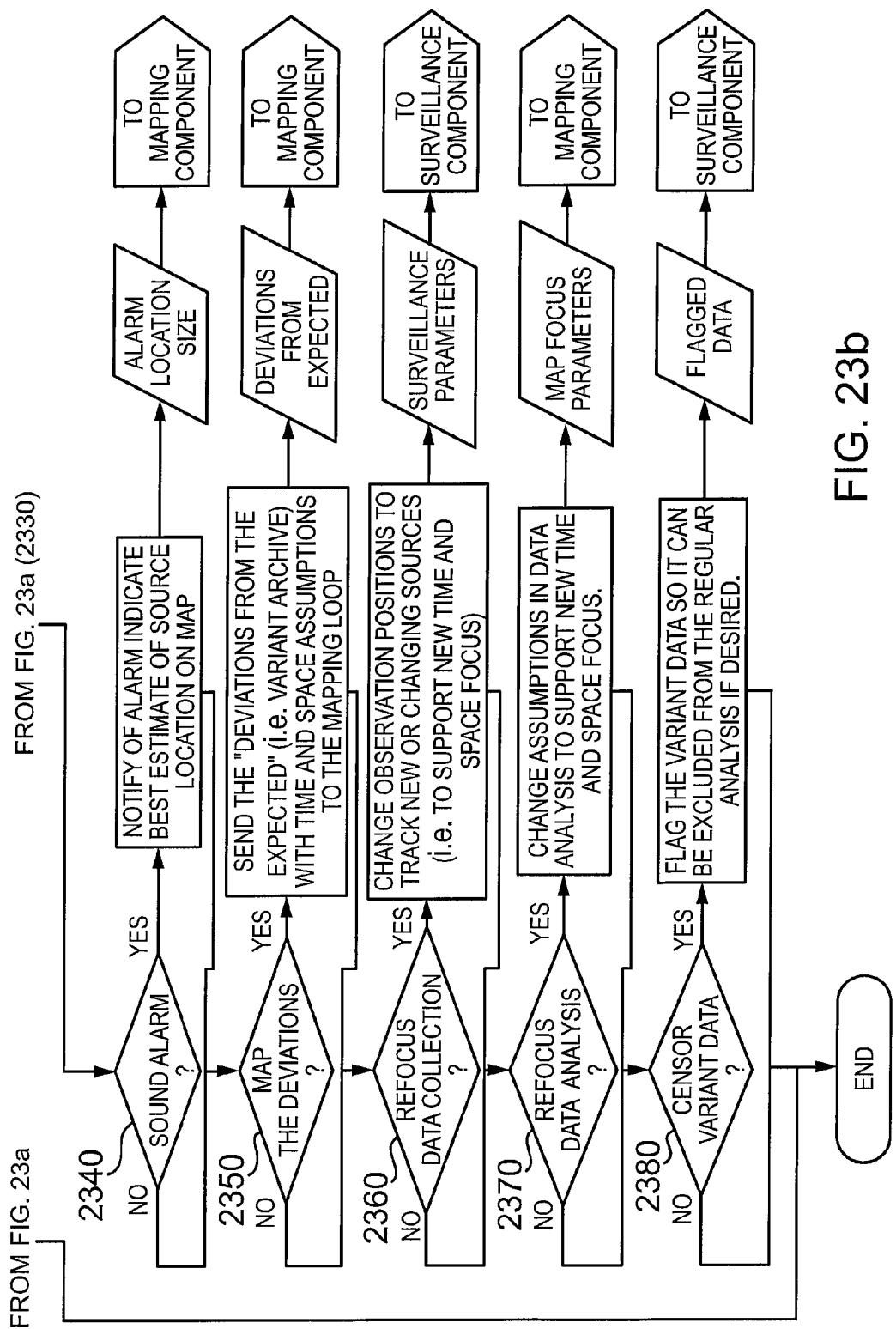

FIG. 22 is a flowchart of a process for mapping an emission source according to an embodiment of the present invention; and FIG. 23a and FIG. 23b are a flowchart of a process for monitoring an emission source according to an embodiment of the present invention.

DETAILED DESCRIPTION OF THE EMBODIMENTS

The detailed description set forth below in connection with the appended drawings is intended as a description of various embodiments of the present invention and is not intended to represent the only embodiments contemplated by the inventor. The detailed description includes specific details for the purpose of providing a comprehensive understanding of the present invention. However, it will be apparent to those skilled in the art that the present invention may be practiced without these specific details.

According to one embodiment, the present invention comprises, as will be described in more detail below, a system and method for locating and characterizing a material or compound (e.g. a contaminant) emitted from one or more sources through the collection of localized measurements (for example, by way of point observations) of concentration data by one or more or more sensors that could be located about an area to be monitored or adjacent to the area and be either moving or stationary and correlating the observed contaminant concentration data to wind speed and direction data (or any other meteorological factors that can affect air movement such as, but not limited to: light intensity, vertical wind speed, temperature, etc.) in such a way as take into consideration wind velocity (i.e. speed and direction) variability along a path (i.e. trajectory) traveled by the emission, e.g. airborne contaminants.

In the context of the present description, a plume means or refers to a column or aggregation of the emitted material which moves through the air. Plume may also refer more generally to a column of a fluid moving through another fluid. Several effects control the motion of the fluid, including momentum, buoyancy and density difference.

As will be described in more detail below, plumes and their trajectories can be identified at an observation point. In the context of the present invention, dimensionless and dimensioned plumes are described. Dimensionless plume boundaries and flux patterns across the cross-sectional area within the dimensionless boundaries can be identified. As will be described in more detail, projecting this information back along the trajectory or path the plume has traveled to the source location provides the capability to predict or determine the dimensioned plume (i.e. the real plume). The dimensioned plume has scalar dimensions that reflect one or more characteristics of the emission, including size, variability, elevation, buoyancy, exit momentum, plume concentration profile and weather point, area or multiple sources. When the location of the source is not known, knowledge of some of its characteristics provide the capability for a single observation point to be used to predict its location, as will be described in more detail below. According to another aspect, multiple observation points are utilized in accordance with the present invention to predict unknown sources based on the agreement in the projected plume information.

The plume boundaries and trajectory are identified in the concentration versus wind velocity plot. The concentration versus wind velocity plot is converted to a flux, i.e. a "flux per unit plume footprint cross-sectional area", versus wind velocity plot. The wind velocity data can be weighted, for example, according to concentration of wind speed, which allows the correct interpretation of concentrations at different wind speeds.

According to an embodiment, dimensionless plumes comprise angular dimensionless measures of the plume boundaries and the flux pattern across the plume is determined at the point of observation. Dimensionless angular width is determined from the peaked flux distribution (for example, as described below for FIG. 10). Dimensionless angular height can be determined either from weighted conversion of wind speeds (for example, as described in FIG. 11) or assumed to be related to the width, or just simply assumed. The boundaries are projected outward along trajectory or path the plume traveled back to the source (not necessarily linear due to curving wind and or obstacles). The dimensionless boundaries are converted to boundaries with scalar dimensions (feet or meters) with the size directly related to distance projected. For example, plume width can be calculated as plume width=sine (dimensionless angular width)*(distance between observation point and projection), and plume height can be calculated in a similar manner.

When projected back the proper distance along the trajectory or path to the source, the true physical size of the plume can be predicted, for example, assuming elliptical or rectangular plume shape, depending on a point source, or an area source or multiple sources. The concentration and flux pattern within the plume boundaries pattern and the "flux per unit plume footprint cross-sectional area" pattern across the plume cross-section can be converted to scalar units, i.e. feet or meters.

According to an aspect, the size of the emitting source can be determined by combining the flux within the plume boundaries less the background flux level measured outside the plume boundary with the area of the plume determined from the scalar dimensions above.

According to an aspect, the variability in the emission rate of the source can be determined by comparing concentrations measured within the plume boundaries to the longer term average concentration pattern profile within the plume boundary, and attributing deviations from the long term average profile to source emission rate changes.

According to an aspect, the elevation of an emitting source can be determining by projecting the trajectory of a plume in the vertical plane back to the source location from one or more observation points.

As will be described in more detail below, by asserting one or more candidates for potential emitting sources, and then determining one or more associated characteristics, i.e. size, variability, elevation, buoyancy, exit momentum, plume concentration profile and weather point, area or multiple sources, by projecting one or more plumes back along one or more plume trajectories (i.e. corresponding to one or more observation positions) provides the capability to predict the presence of one or more emitting sources based on the agreement, e.g. convergence, of the one or more candidates for potential emitting sources.

In addition to plumes or segments of plumes, individual readings or groups of readings (and associated flux per unit cross-sectional footprint area) can be projected back along the trajectory or path traveled from a single, multiple or mobile observation points to determine one or more potential emission source locations. The existence of one or more emission sources can be asserted, i.e. determined, based on agreement from the observations, e.g. multiple observations from a single position over time, or observations from multiple positions or observations from mobile points.

Sampling Setup

In accordance with an embodiment of the invention, air concentration measurements of a particular emission, for example, an air contaminant, can be collected at multiple locations about an area of interest. Multiple measurements can be collected by using a single sensor, multiple stationary sensors, one or more moving sensors, or one or more stationary analyzers that draw air samples from spaced apart locations. The area being monitored can vary from very small in the range of 10's of meters to very large, e.g. greater than 10's of kilometers (the range limit is unknown). The larger the area to be monitored, the more the air contaminant concentration measurement locations have to be spaced from each other to improve triangulation. For certainty, while the locus of the air contaminant concentration measurements defines an inner area, spacing the measurement locations from each other, also enables detection of contaminant sources outside the locus.

Figure 1:
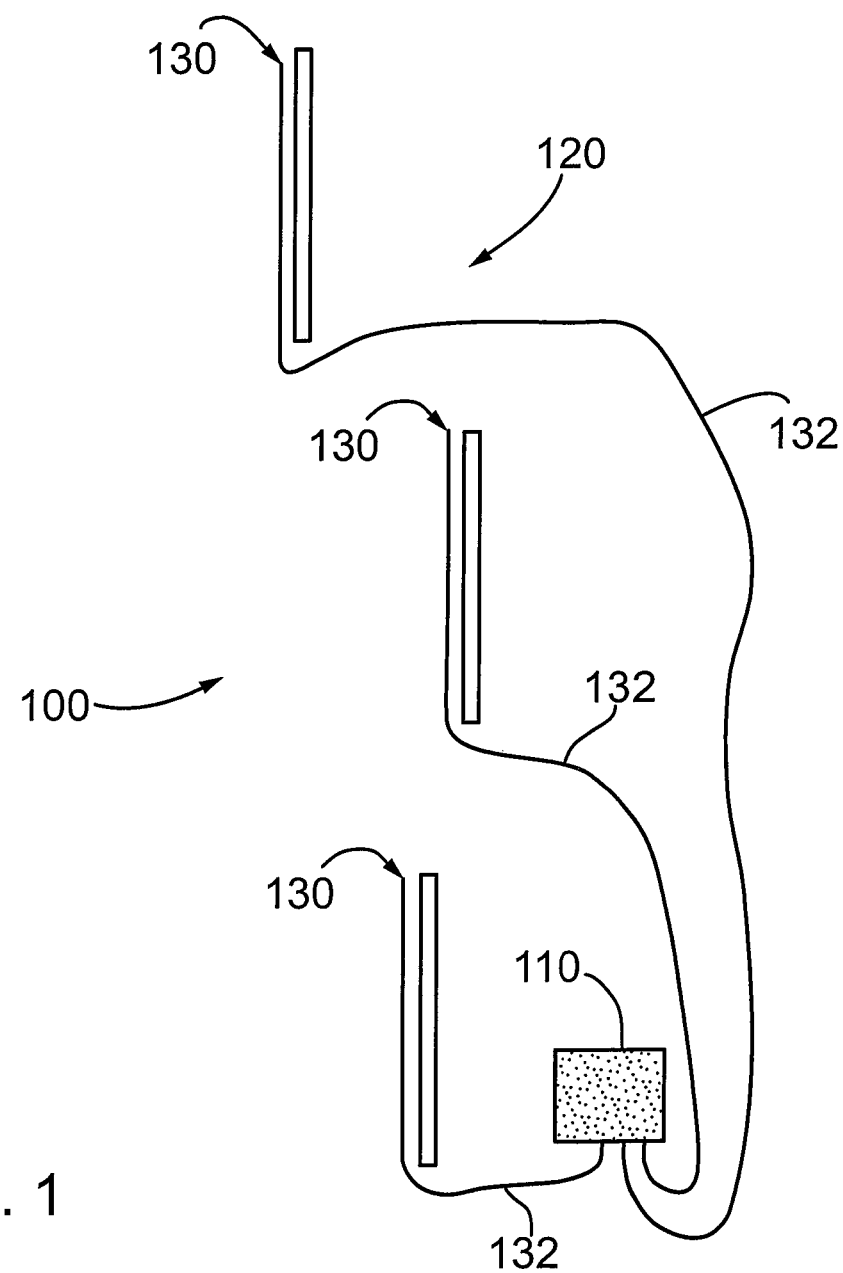
FIG. 1 is a schematic diagram showing an air sample monitoring system in accordance with an embodiment of the invention.

FIG. 1 shows an air sample monitoring system 100 having an equipment package 110 servicing a group 120 of sample inlets 130 in accordance with the embodiment of the invention.

Air samples are drawn from each sampling inlet 130 down sample lines 132 which may include small diameter tubing (plastic or the like), to the equipment package 110. The sample inlets 130 can be positioned anywhere with respect to the equipment package 110. However, the cumulative friction between the air samples within the sample lines 132 and the sample line walls may limit the length of sample lines 132. Also different compounds have different wall adhesion largely depending on compound molecular size and weight, and therefore different compounds take a slightly different time to travel along a sample line. The actual time of travel down a sample line can be determined empirically.

Figure 2:
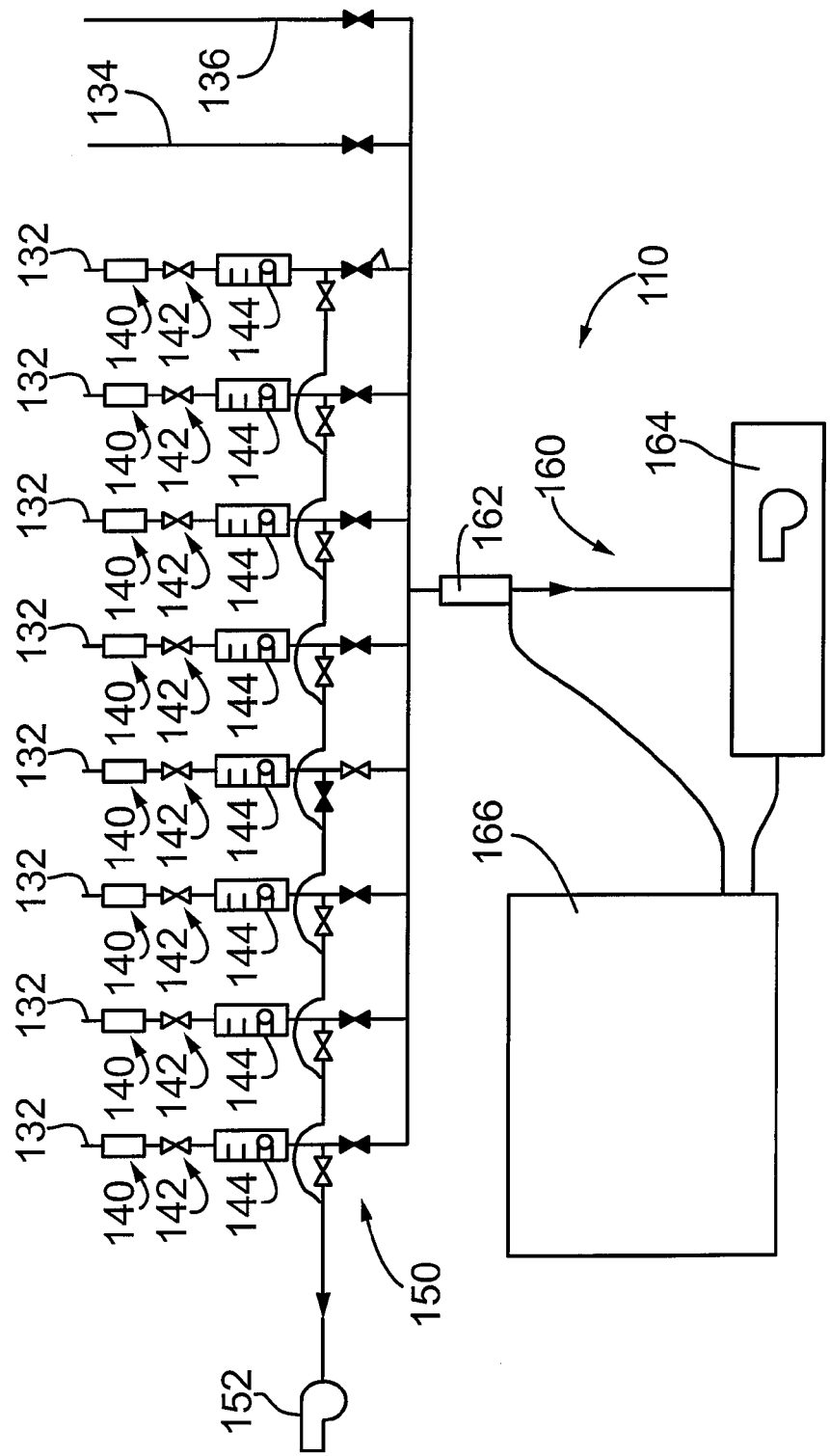
FIG. 2 is a schematic diagram showing elements of an air sample analysis system in accordance with the embodiment of the invention.

FIG. 2 shows elements of an implementation of an air sample analysis system in accordance with the embodiment of the invention, the equipment package 110 includes:

sample lines 132 configured to convey air samples from corresponding sampling inlets 130, each sampling line 132 may include:

a filter 140 configured to filter out debris (filter could be put at inlet end of sample line to keep debris out of sample line as well);

a (needle) valve 142 configured to control the rate air intake; and a flow rate sensor 144 configured to provide a flow rate output for valve 142 adjustment;

a zero line 134 configured to supply zero gas;

a span line 136 configured to supply gas having a know concentration of the target contaminant to be detected;

a valve manifold 150 configured to couple a selected air sample flow from one of the sample lines 132 to a sample analysis stream 160;

a vacuum source 152 configured to draw air samples via the air sample inlets 132 and thereby to convey the air samples to the equipment package 110;

an flow meter 162 configured to measure the flow rate of the air sample in the analyzer stream 160;

at least one sample analyzer 164 configured to receive an air sample from the sample analysis stream 160 and to perform a measurement on the air sample, such as but not limited to, measuring the concentration of a particular compound (the sample analyzer may include its own pump); and a controller 166 configured to actuate valves of the valve manifold 150, activate the at least one analyzer 164, receive and log data including, but not limited to: an indication of which air sample stream is being analyzed in the sample analysis stream (valve position), sample flow rate, concentration, sample analysis time, wind speed and wind direction.

In accordance with an implementation according to an embodiment of the invention, the controller 166 is further configured to log sampling times. Due to non-trivial lengths of the sampling lines 132, the controller 160 may be further configured to take into account the propagation delay of each air sample along the sample line 132. For such a purpose, the controller 160 may employ the flow rate output provided by the flow meter 162, the inner diameter of the sample line 132 and the length of the sample line 132 to provide an estimate of the time of travel of each air sample from the sample inlet 130 to the sample analyzer 164 at the equipment package 110.

For continued air monitoring applications, a fresh air sample may be necessary for each air sample analysis performed by the sample analyzer 164. Particularly in view of long sample lines 132, fresh air samples can be applied to flush or otherwise remove stagnant air in the sample line. When multiple sample lines 132 are connected to the equipment package 110, a fresh air sample may only be required during the time period when each sample line 132 is selected and connected to the sample analysis stream 160.

Without limiting the invention, having fresh air samples for analysis may be achieved, for example, by continuously drawing air samples to avoid the time delay to clear the sample line 132, or by initiating the drawing of an air sample sufficiently in advance of the sample analysis to clear the previous sample from the sample line 132. When not connected to the sample analysis stream 160, sample lines 132 may be connected to the vacuum source 152 to maintain a constant flow to deliver fresh air samples down the sample lines 132 while each sample line 132 waits its turn to deliver an air sample to the sample analysis stream 160, which may deliver the sample at a constant flow rate. The vacuum source can include a vacuum pump, and the length of the sample lines 132 may be limited by the ability of the vacuum pump to draw air samples through the sample lines 132.

Without limiting the invention, each sample line 132 can be selected in accordance with a selection discipline, via the selection valve manifold 150, to be coupled to the sample analysis stream 160. Depending on the particular implementation, the valve manifold 150 can include solenoid valves, for example, a series of 2/2 way valve pairs, or a series of 3/2 way valves.

Optionally, the flow rate meters 144 may include rotameters employed to provide visual confirmation of air flow down the sample lines 132.

The equipment package can be retrofitted to existing air monitoring equipment by connecting the sample analysis stream to the existing air monitoring equipment.

Second Prototype of Hardware Package

For some configurations of the equipment described above, the assumption of constant and stable flow in the sample lines 132 may not hold, and measuring only the flow rate in the sample line 132 that was delivering a sample to the sample analysis stream 160 may not be completely accurate. Therefore adjustments may be necessary for any flow rate changes that may occur on the sample lines 132 during valve changes or longer term declines in flow rates due to pump wear-out.

Figure 3:
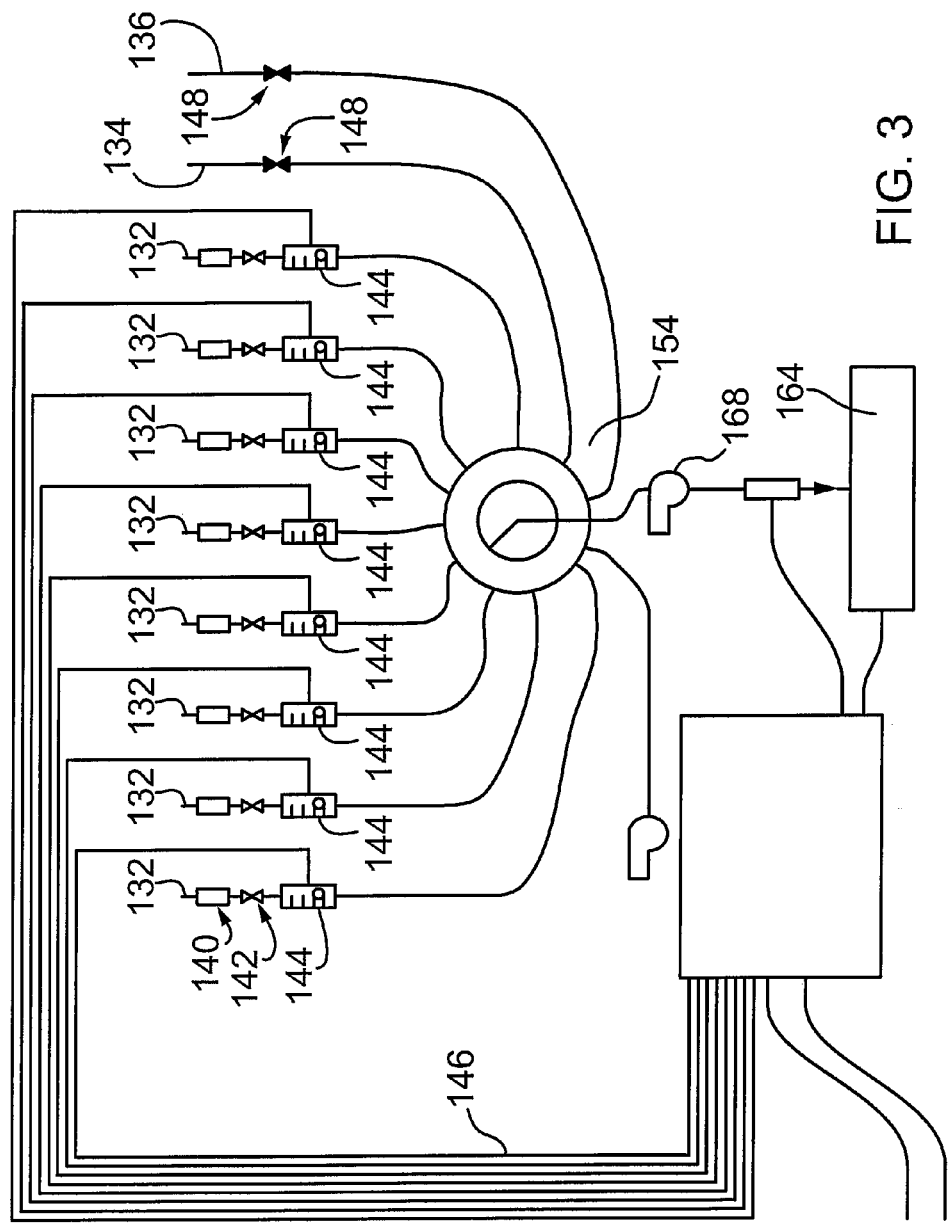
FIG. 3 is a schematic diagram showing elements of an air sample analysis system in accordance with another embodiment of the invention.

FIG. 3 shows elements of another embodiment of the equipment package 110 which includes:
  a multi-port valve 154 (for example VICI valve number "H-EMT2SC16MWE" available from VICI Valco Instruments Canada Corp., 26 Water Street East, Brockville, ON K6V 1A1, Canada, Phone: (613) 342-2600, Toll free: (866) 297-2626, Fax: (613) 342-0111, canada@vici.com, www.vici.com) having inputs to which at least some of the following connect:
    the sample lines 132,
    the zero line 134, and
    the span line 136;
  and outputs including:
    a common bleed line connected to the vacuum source 152, and
    a line leading to the sample analysis stream 160;
  a sample analysis stream pump 168 configured to draw an air sample via the sample line 132 selected via the multi-port valve 154 to be connected to the sample analysis stream 160;
  signaling lines 146 connecting each flow sensor 144 to the controller 166, the controller 166 being further configured to adjust valves 142 to match sample line flow rates to a common flow rate selected for all the sample lines, for example to match the flow rate of the sample analysis stream pump 168;
  solenoid valves 148 on the zero and span lines configured to shut off the zero and span gases when not in use to conserve zero and span gases (as opposed to the air samples, the zero and span gases do not vary in concentration).

Remote Sampling

In accordance with the embodiment of the invention, locations for a group of sampling inlets 130 about the area of interest are selected. According to an embodiment, the sampling locations are separated from each other to provide for triangulation in locating contaminant sources that may exist within or without the air-sampling locus.

Sample inlets 130 positioned at several elevations may be employed; at least one sample inlet positioned at least as high as the elevation of the highest potential leak may ensure that emission plumes would not pass by the sample inlets 130 undetected.

In accordance with an implementation according to an embodiment of the invention, remote sampling couplets can be employed. Each sampling couplet can include at least two sampling inlets 130 preferably having a broad geographical separation and coverage of the area of interest. Accordingly sub-groups of groups of sampling locations may be established which provide coverage for different sized monitored areas and at different distances. For example, for large contaminant emissions released at great distances from the sample measurement locus, each couplet functions as a point measure, while at the same time providing surveillance for smaller contaminant leaks released closer to the sample measurement locus.

Calibration

As an initial step, a calibration of the analyzer 164 is performed. The analyzer 164 can also be calibrated at selected interval (for example, once a day). The calibration involves providing a (gaseous) sample that is known to be free of the compound to be detected and recording the analyzer's response (called the zero reading) followed by the provision of another sample containing a known concentration of the compound to be detected and recording the analyzer's response, i.e. the span reading.

In order to obtain the zero response, the valve manifold 150 or the multi-port valve 154 and valve 148 on the zero line 134 are configured to connect the zero line 134 to the sample analysis stream 160 and turn the zero gas on. In order to obtain the span response, the valve manifold 150 or the multi-port valve 154 and valve 148 on the span line 134 are configured to connect the span line 136 to the sample analysis stream 160 and turn the span gas on.

Calibration adjustment factors are obtained by comparing the recorded zero and span responses of the analyzer 164 to true values, for example, 0 and 100 ppm. The instruments response can be corrected internally to the zero and span reading.

Data Collection

Data collection follows calibration, which can occur periodically during data collection. FIG. 4 shows tabulated raw data collected every 10 seconds employing a stationary sensor setup wherein the location of the sample inlets 130 does not change during the data collection. Valve positions correspond to pre-assigned sample inlet locations in terms of latitude, longitude and elevation for stationary sample inlets 130. FIG. 5 shows tabulated raw data collection using a (mobile) sensor setup, each entry including: latitude, longitude, and elevation. A log of wind speeds and directions are kept, from which a previous wind speed measurement and a corresponding wind direction measurement may be selected based on the air sample propagation time delay down a corresponding sample line 132, valve manifold 150, sample analysis stream 160 and possibly through at least a portion of the analyzer 164.

The invention is not limited to a 10 second data collection interval, data collection frequencies may range from less then 0.5 seconds to hours. The concentration data readings are averaged during an interval of sampling to reduce signal noise and possibly analog to digital conversion errors. For example, measurements can be made at a frequency of 500 readings per second collected and averaged over the 10 second period. Contaminant concentration can be measured in parts-per-million (ppm). The concentration data collected during a calibration interval can be adjusted with the calibration readings obtained for that calibration interval either by the sample analyzer 164 or as a post-measurement processing step performed by the controller 166.

As valve positions change for a different sample line 132 to be connected to the sample analysis stream 160, a transition period is employed during which at least the sample analysis stream 160, and the analyzer 164, may be purged of the previous air sample held therein. Any readings taken during the transition period are discarded, or measurement reading may be paused for the duration thereof. Any sampling strategy to improve the detection limit of the detectors can be used like drawing a large sample through an absorbant and then periodically desorbing.

Calculating Wind Direction

In tracking emission sources an accurate characterization may be needed of air movement (wind driven) driving contaminant plumes from emitting sources to the air sample inlets 130 at corresponding measurement locations. In accordance with the embodiment of the invention, wind speed and wind direction are not assumed constant, and actual wind speed and wind directions are included in determining the location of contaminant sources. As described above, wind speed and direction can be measured at each air sample inlet 130 location or at a reduced number of locations. Following the measurement of wind velocity characteristics such as, but not limited to: wind speed and direction readings, the wind characteristics are correlated with the corresponding concentration readings performed by the at least one analyzer 164. Correlating wind characteristics can take into account air sample travel time along the sample lines 132 from the air sample inlet 130, and time of travel over the area of interest.

By way of example and without limiting the invention, wind speed is provided by a wind meter as the rate of rotation of a wheel spun by the wind, and wind direction may be provided by the output of an encoder encoding the orientation of a wheel connected to a wind vane. Both outputs may be provided to the controller 166 as described above, typically as electronic signals whether analog or digital. Depending on atmospheric conditions, vertical wind speed is also taken into account.

Wind Direction Correction

The accuracy of the triangulation may depend on the accuracy of the wind direction measured. Several aspects of wind direction may need correction: internal errors of the wind meter, external errors of the wind sensor and possibly adjusting the reading from the output range to the zero-to-360 range.

Internal corrections: for a wind sensor employing a potentiometer to encode the direction of the wind vane, when the wind vane is pointed at North there can be internal errors in the positioning of the potentiometer and other electronic components that measure direction which would result in the output not equating 360 degrees. There are additional errors that can result in the electrical signal (current or voltage) from the wind sensor and recorded in the data file. The correction needed is determined by connecting the wind sensor in the field to the length of cable and data logger that will be used in the setup (this ensures that any shifting or degradation of the electrical signal are included in the calibration) and then the wind vane positioned at the know positions of North, South, East, and West as accurately as possible. Some wind sensors use a dual potentiometer encoding system that records wind direction from 0 to 540 degrees, in this case the sensor may be rotated to record the output at each 90 degree interval (i.e. 0, 90, 180, 270, 360, 450, and 540). A correction value is determined by plotting the expected and the actual readings, this correction typically has the form $y=mx+b$ and in some situations it is possible that m will be 0 so the correction will be a constant that is applied to all the readings.

External Correction: the external correction is provided because when positioning and securing the wind sensor in the field it is impossible to have it pointing exactly in the right direction and an adjustment is generally required. The size of the adjustment needed is determined by sighting along the vane at some distance (100's of meters) and finding where the North (and/or South) direction is pointing and measuring the distance off true north or south and calculating the number of degrees required to correct the readings. This correction may typically be a constant correction.

Adjustment: if the readings beyond 360 degrees are reported, these may be converted or adjusted back to the 0-to-360 range.

Figure 6:
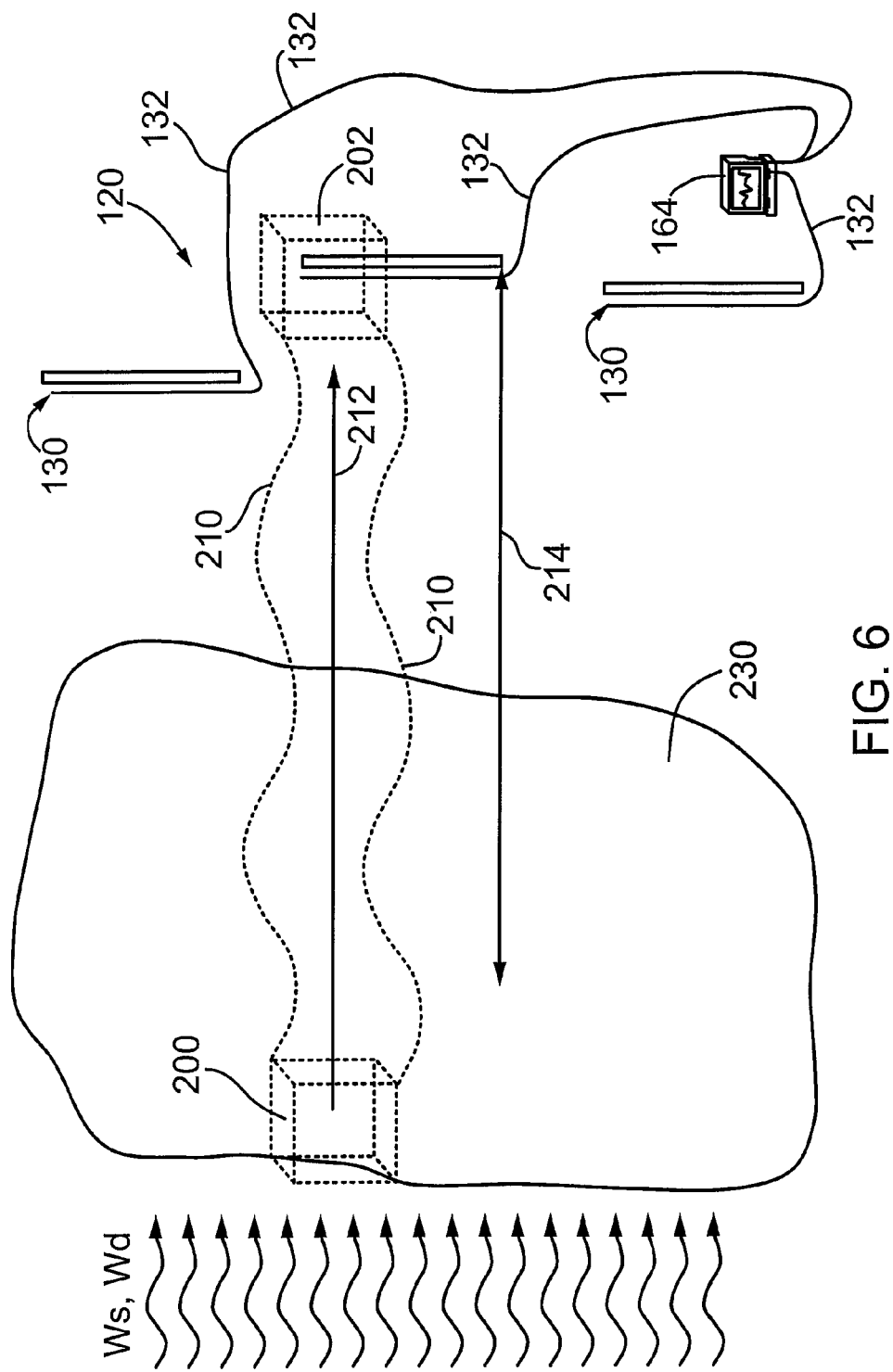
FIG. 6 is a schematic diagram showing variables taken in to account in correlating wind speed and direction data to corresponding analysis measurements.

FIG. 6 summarizes the wind measurement assignment calculation required to correlate the wind speed and direction data to the corresponding concentration readings.

The wind speed and direction is not stable over time and can vary second to second moving a volume of air 200 along a nonlinear path 210 from an area of interest monitored for the existence of a contaminant source to a sample inlet 130. Obstructions such as land topography and buildings can cause wind to be non-linear, and knowledge of the geometry of such obstructions can improve the tracking of the trajectory of the air. Accordingly, wind speed and direction estimates are related to individual readings from the analyzer 164. The frequency of readings can be as high as once every second or every half second because it was found that plumes are being shifted by the wind effects at this time scale. The analyzer readings reflect contaminant compound concentration in a volume of air 202 that has traveled through the analyzer 164, down the sample line 132, aspired from the volume of air (200 that has been blown over the area of interest 230 entraining molecules of the contaminant compound emitted from unknown contaminant emission source(s) in the area of interest 230. Readings from the analyzer 164 are related to wind sensor readings.

In accordance with an embodiment of the invention, a higher level process is provided to account for the wind variability by back tracking the nonlinear path 210 of the volume of air 202 from the sample inlet 130 back over the area of interest 230, by stepping backward in time and outward in space away from the sample inlet 130 adjusting the path and concentration with each step for the changing wind conditions (note concentrations would be adjusted to reflect the dispersion that occurs as the plume travels down wind). Each contaminant concentration measured by that analyzer 164 takes into account the degree to which changes in wind velocity have affected the air sample traversing the path 210 outward and up-wind from the sample inlet 130. The concentration of a contaminant increases along path 210 as it is traversed backwards towards the source due to the (natural) dispersion that occurs. A mapping technique lays out a high number of paths generated with high frequency sampling (i.e. roughly 100 thousand per day, per sample inlet 130 location at one second sampling) from multiple remote sampling inlets 130. Combining all the paths that traverse through each plot of land being mapped and averaging concentrations along such paths 210 corresponding to the all the paths from the different sample inlets 130 can be employed to predict the location(s) of contaminant emitting source(s). Paths 210 with high compound concentrations congregate at plots of land that contain emission sources.

In accordance with another embodiment of the invention, and as a simplification of the above a representative wind velocity is employed wherein the non-linear path 210 can be replaced with the linear vector 212 which estimates the average wind (velocity) speed and direction during the time of travel of the volume of air 200 from area of interest 230 to the sample inlet 130. A measure of the standard deviation of wind speed and direction is also calculated to provide an estimate of the accuracy of the assumption of linearity of the nonlinear flow path 210. The linearity assumption can have more error at low wind speed because of longer averaging times and possibly due to a more unstable direction of flow of the wind (i.e. low speed wind may be subject to more radical changes in direction than high speed wind. In addition the travel time, which is calculated as the distance 214 over wind speed, increases dramatically as a function of reciprocal wind speed and at low speeds (i.e. air moving at low speed takes much longer to get to the sampling inlet 130 and results in a longer averaging time substantially equal to the traveling time). The result of standard deviation calculation is used to filter out readings of the analysis that occur when the wind direction shifts too much for an accurate prediction of the flow path 210/212. This technique identifies wind data that accurately predicts wind effects and eliminates data that does not. Accurate low wind data may be very valuable in locating emission sources at great distances if the wind direction is stable. With knowledge of the geometry of the topography, buildings and other obstacles, the trajectory of the plume can be assumed linear and corrected for movement around obstacles. With this technique, an estimate of the distance 214 from the area of interest to the sample inlet 130 is used to determine the duration of averaging needed. It was found that the distance to the monitored area may be fairly rough. An accuracy (±50%) of the assumed distance does not seem to have an important impact on the prediction of the average representative wind velocity because; at high wind speed the wind direction is more stable, and at low wind speed because averaging times are so long that the variability in low wind direction averages out. A rough first guess of the distance can be used to identify sources and then a much better distance estimate to each source obtained. In an iterative fashion, the data can be analyzed again using the better distance measures to each source to focus the analysis better (maybe even increasing the wind direction increments to one tenth of a degree accuracy in the follow up runs). This focusing can serve to improve the location, sizing and characterizing of the sources.

In accordance with another embodiment of the invention, an iterative approach is provided, wherein a rough initial estimate of distance is used to establish a first estimate of the distance to emission source(s) and then a more accurate distance is calculated and used in another run.

As a subsequent step, an adjustment is made for the time of travel of the air sample 202 from the sample inlet 130 location down the corresponding sample line 132 through the equipment package 110 and to the analyzer 164. The time of travel of the air sample 202 down the sample line 132 may be measured empirically by aspirating a sample 202 of known concentration at the sample inlet 130 and timing the length of time need for the analyzer 164 readings to respond with the arrival of the air sample. Alternatively the internal volume of sample line 132 (cross-sectional area of the sample line multiplied by the length thereof) can be divided by the sample flow rate drawn through the sample line 132 and adding the time needed for the analyzer 164 to respond to a sample that enters the analyzer 164. The time of travel of air samples down the sample line 132 are typically unique to each valve position.

Figure 7A:
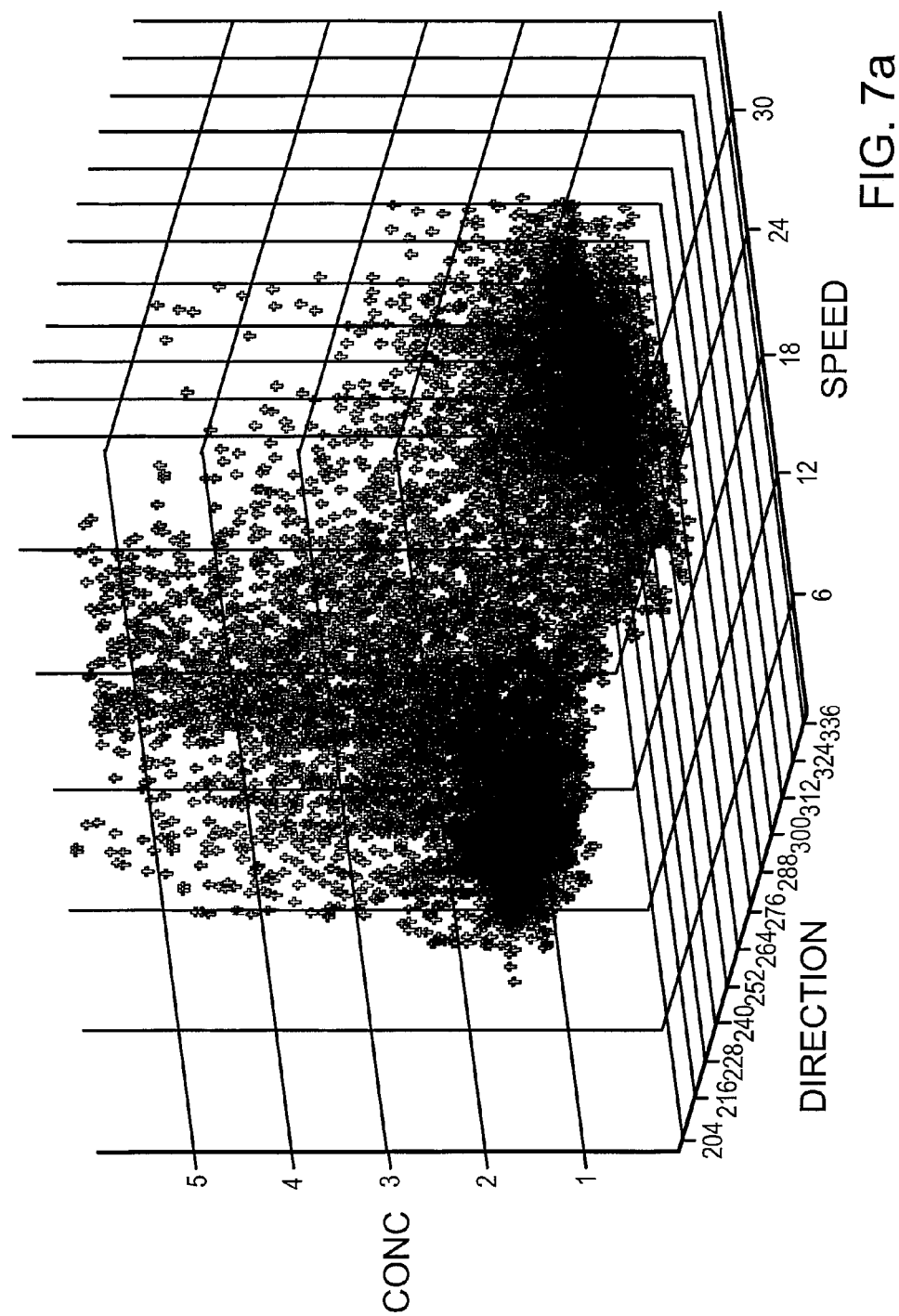
FIG. 7a, FIG. 7b, and FIG. 7c are a sequence of graphs showing data processing in obtaining a variation of average material concentration.
Figure 7B:
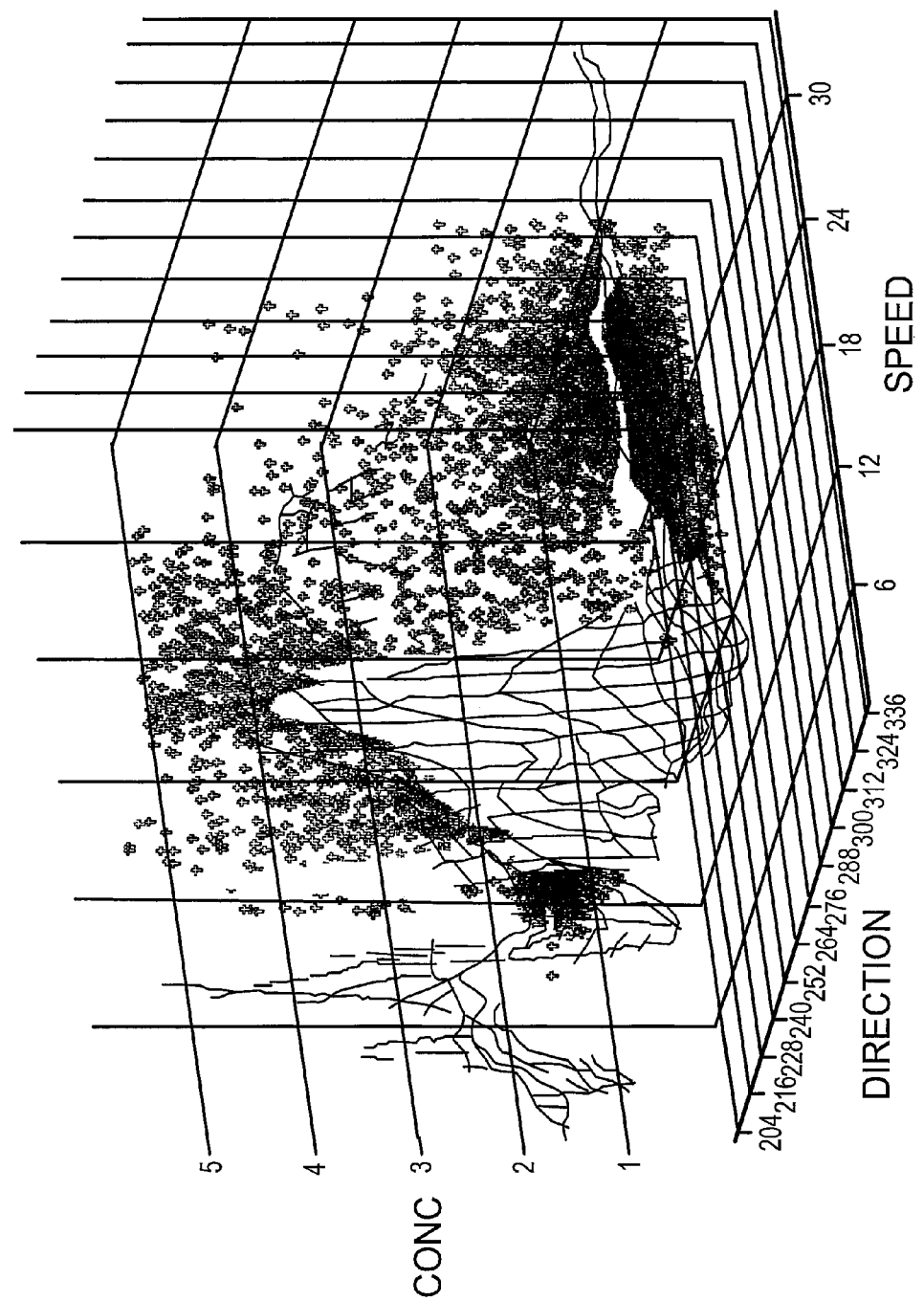
Figure 7C:
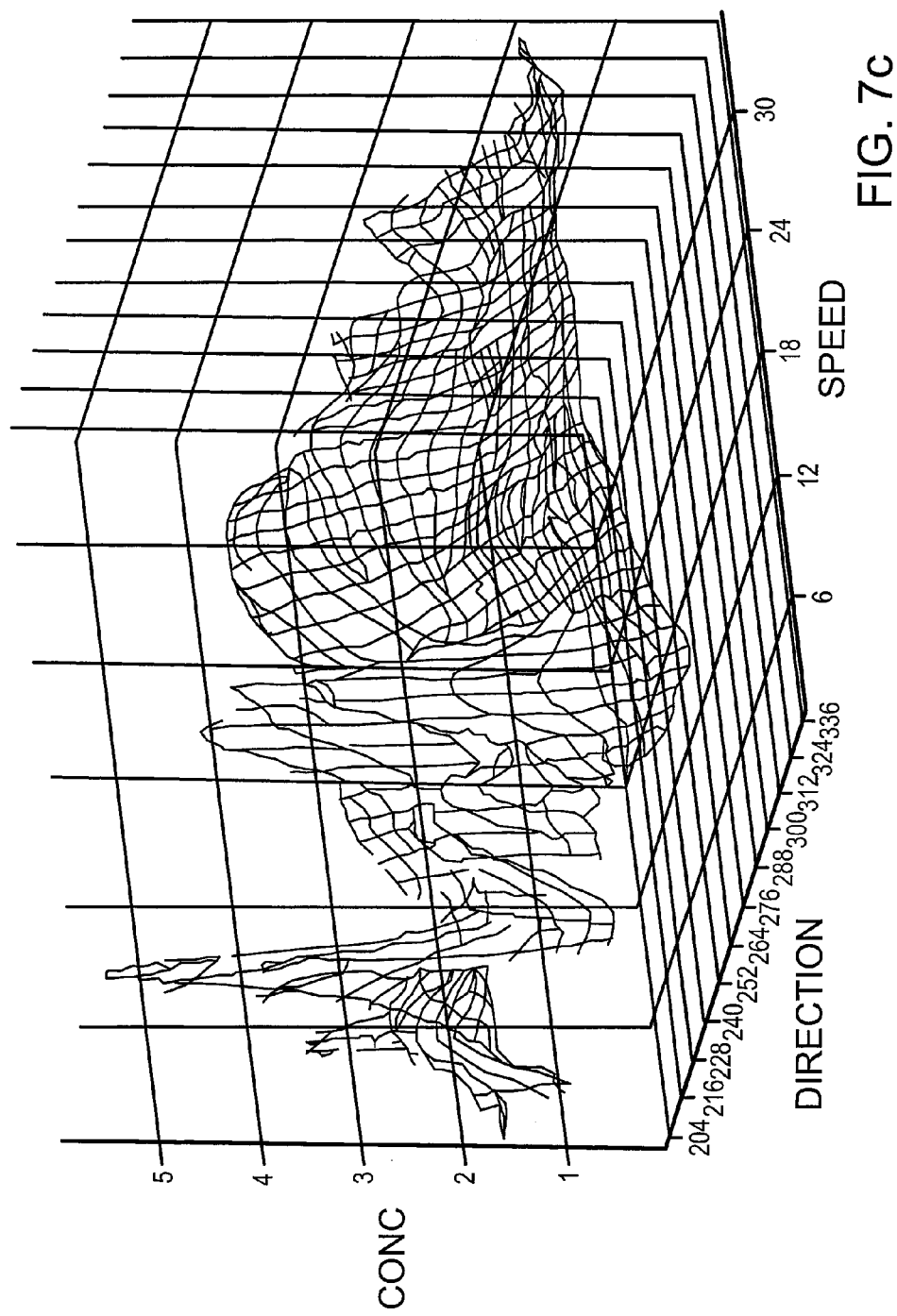
Figure 8A:
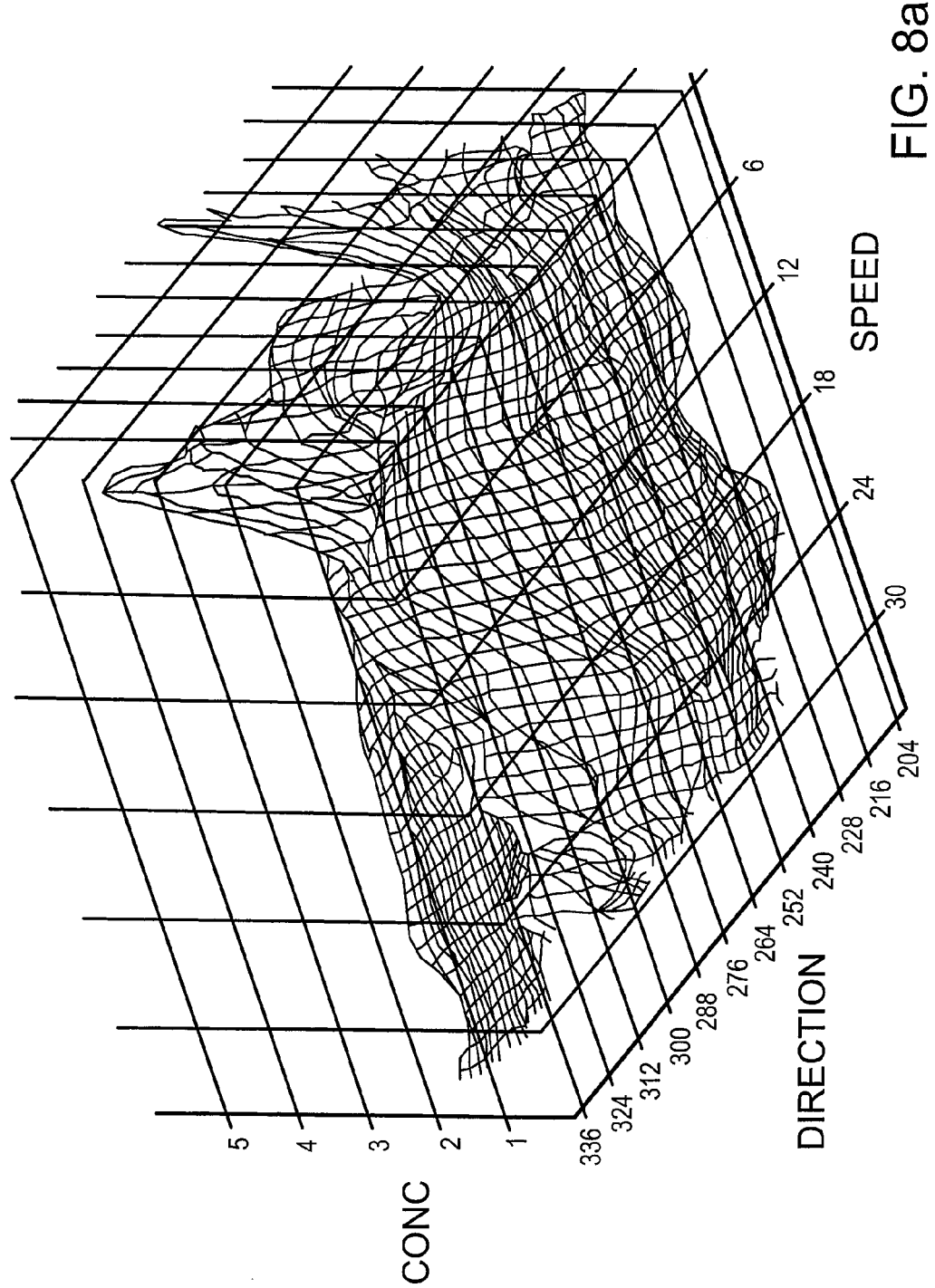
Figure 8B:
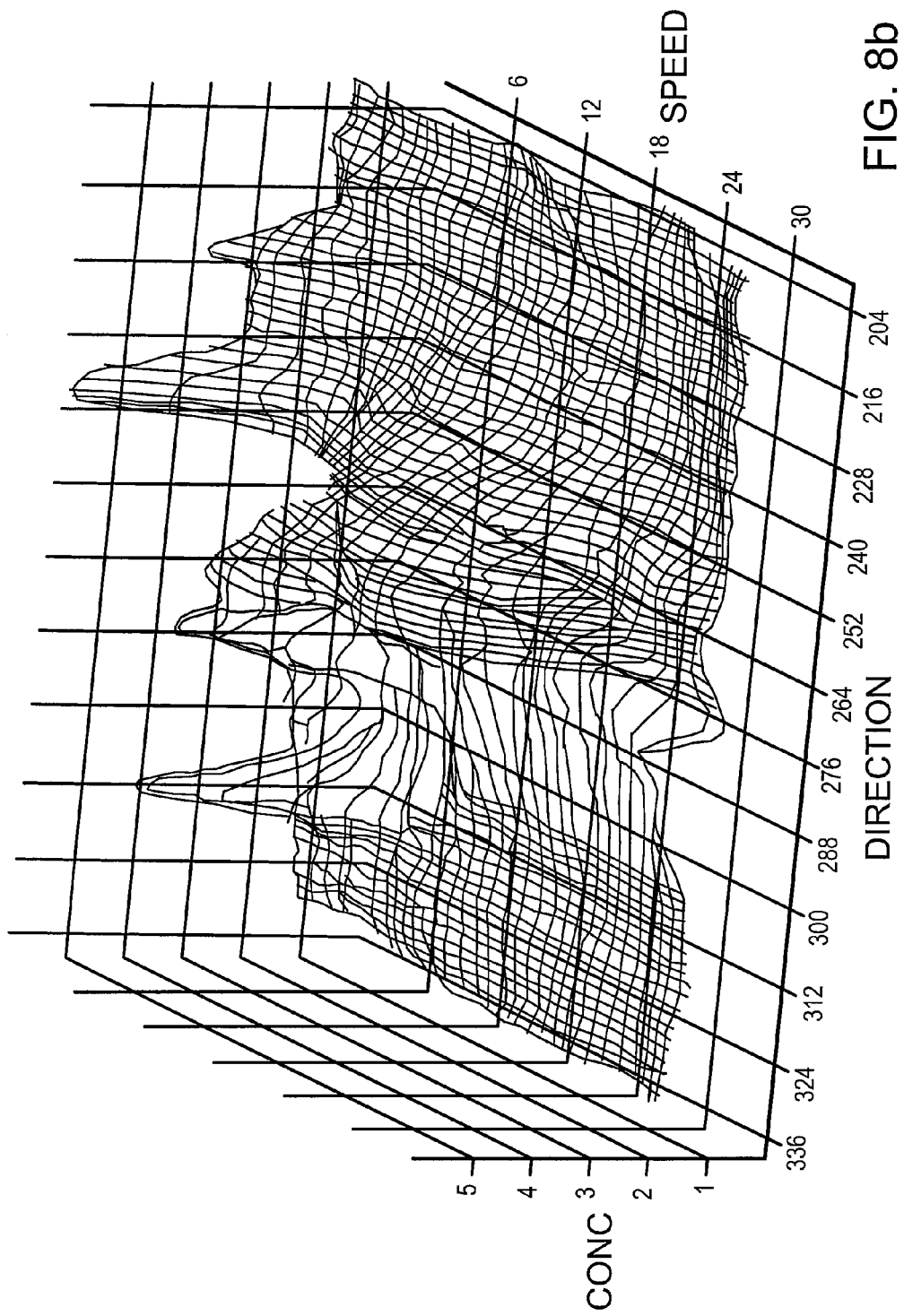

In accordance with an implementation the analyzer 164, contaminant concentration readings are related to wind speed and direction at a corresponding inlet 130 as follows:
each concentration reading relates to a representative wind vector (t–t1 to t–(t1+t2)) given that:
130—Remote sample inlets
200—Hypothetical volume of air traveling from area of interest to remote inlet.
210—Non-linear path of the volume of air driven by the wind
Ws—The wind speed
Wd—The wind direction
212—Average wind vector (speed, direction) during travel time (t–t1 to t–(t1+t2))
164—Analyzer detector
214—Distance from area of interest to remote sample inlet
132—Sample tubing running from remote sample inlet 130 to analyzer 164
230—Area of interest
t—Current time
t1—travel time of sample from the inlet 130 to the sample analyzer 164=(sample tube volume)/(flow rate)
t2—travel time of 200 from area of interest 230 to the sample in 130 divided the representative wind speed Populating the Table of Wind Speeds and Directions In a subsequent step the variation of concentration of the contaminant with wind speed and direction is determined. FIG. 7 shows concentration readings plotted against wind speed and direction in a three-dimensional plot. FIG. 7 shows an average surface through the cloud of data, and FIG. 8 shows average concentration surface without the data points. The average (or median) contaminant concentration variation surface reflects plume characteristics, the figure showing the association of low wind conditions with high contaminant concentrations, and contaminant concentration decreasing with increasing wind speed unless the wind is blowing in the direction of a contaminant source, in which case contaminant concentration decreases with separation distance and increases with wind speed.

Each mapped contaminant can have a corresponding surface for each sampling inlet location. For example, drawing air samples at six sampling inlet locations and employing three analyzers 164 measuring corresponding contaminant concentrations would result in 18 such graphs. For example, the surface shown in FIG. 8 was generated from data collected over 5 weeks worth of measurements averaged over 10 second intervals and plotted.

Making reference to FIG. 6, concentration measurements are converted into a surface.

As an initial step, for each compound analyzed and for each remote sample inlet a set of bins/registers is defined, bins which store concentration data measurements for every combination of wind speed and direction. For example if wind between 0 to 50 kph is considered using a resolution of one kph increments and wind direction from 0 to 360 degrees using one degree increments, then 18,000 (360*50) registers or bins to allow for every combination of wind speed and direction.

Each recorded reading from the analyzer 164 is assigned to a bin based on the contaminants measured, the remote sampling location, and the representative wind speed and direction that affected the volume of air that the sample was drawn from as it traveled over the area of interest to the remote sampling inlet. The data sets generated previously are stepped through one record at a time and each concentration reading is assigned to the appropriate bin.

Digital values of the surface at all wind speeds and direction are obtained by averaging (or median) the concentration measurements accumulate in the bins. An adequate (large) number of concentration measurements are required in each bin to obtain an average and digitized surface due to the unstable nature of the air concentration measurements. This unstable nature is evident in the earlier FIG. 8 where the average level in the surface is plotted along with individual measurements wherein the individual concentration measurements are shown scattered well above and below the average concentration surface.

Adjusting the Digital Surface

The adjustments may need to be made to the average contaminant concentration surface on the assumption that at a low resolution, the true surface is continuous and smooth without step changes in concentration with varying wind speed and direction. The surface should be generally continuous due to the dispersion of contaminant in the emission plumes as the air travels from the contaminant emission source to the sampling inlet location. A reasonable assumption because essentially stating that the concentration at one wind speed and direction is linked to the concentration at the same wind speed but one degree difference. This means that the true concentration measured in respect of a bin should be similar to that of the neighboring bin.

Based on the above assumption, readings stored in neighboring bins of the registry can help predict the true valve of the surface at a bin. The adjustment combines the readings stored in a bin with the measurements held in neighboring bins (this is done via preset adjustable intervals, for example, three bins along increasing and decreasing wind direction and four bins in along increasing and decreasing wind speed). The larger the interval the more smoothing of the true surface will occur. Smoothing can reduce the noise in the data but may also round off any sharp characteristics in the actual surface.

In order to reduce deleterious smoothing of the true surface that occurs with the above adjustment, one can employ average weighting techniques taking into account proximity of bins being considered giving more influence to neighboring bins which are closer in wind speed and direction to the bin in question.

In order to characterize contaminant emitting sources only, the background concentrations of the contaminant monitored are subtracted from the average concentration surface.

Calculating Flux Per Unit Area

Flux is fluid flow past a surface. An emitting source generates a contaminant plume driven by the air movement and expanding due to dispersion. As the plume crosses a boundary, the rate of contaminant flow or flux of the contaminant through the boundary corresponds to the emission rate of the contaminant as long as the emission rate is constant assuming that contaminant is not being created nor destroyed as it travels. The flux of a contaminant plume is employed to quantify the emission rate of a corresponding emitting source. The product between contaminant concentration and wind speed give an indication of flux per unit area. If the area of the plume passing the boundary was known, then flux=concentration*wind speed*plume area. Each plume may be approximated with a suitable shape, for example, a conical plume, in nature not necessarily of a circular perpendicular cross-section.

Figure 9A:
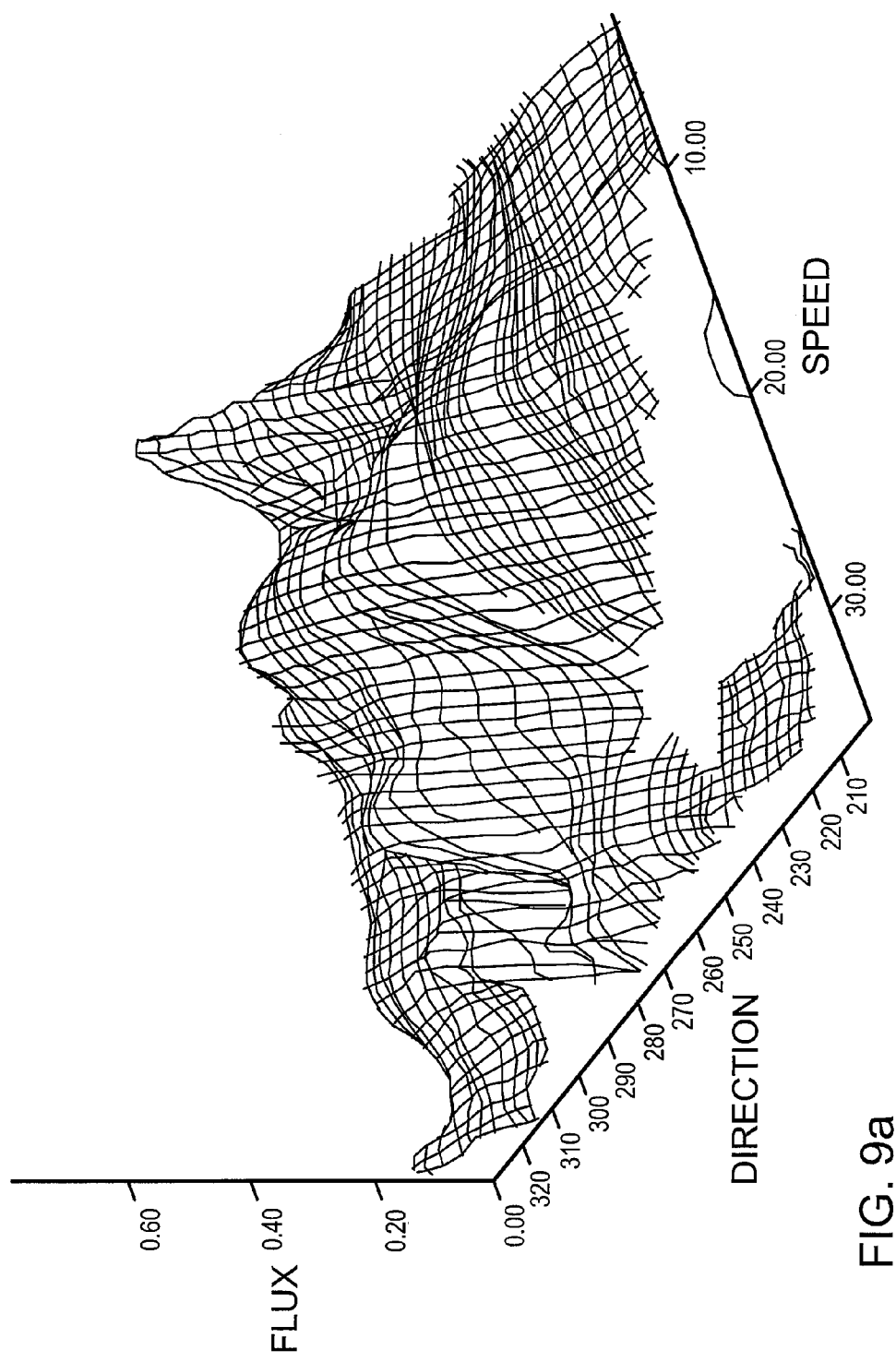
FIG. 9a, FIG. 9b, and FIG. 9c show different perspectives of a variation of flux per unit plume footprint cross-sectional area plotted versus wind speed and direction shown in FIG. 8.
Figure 9B:
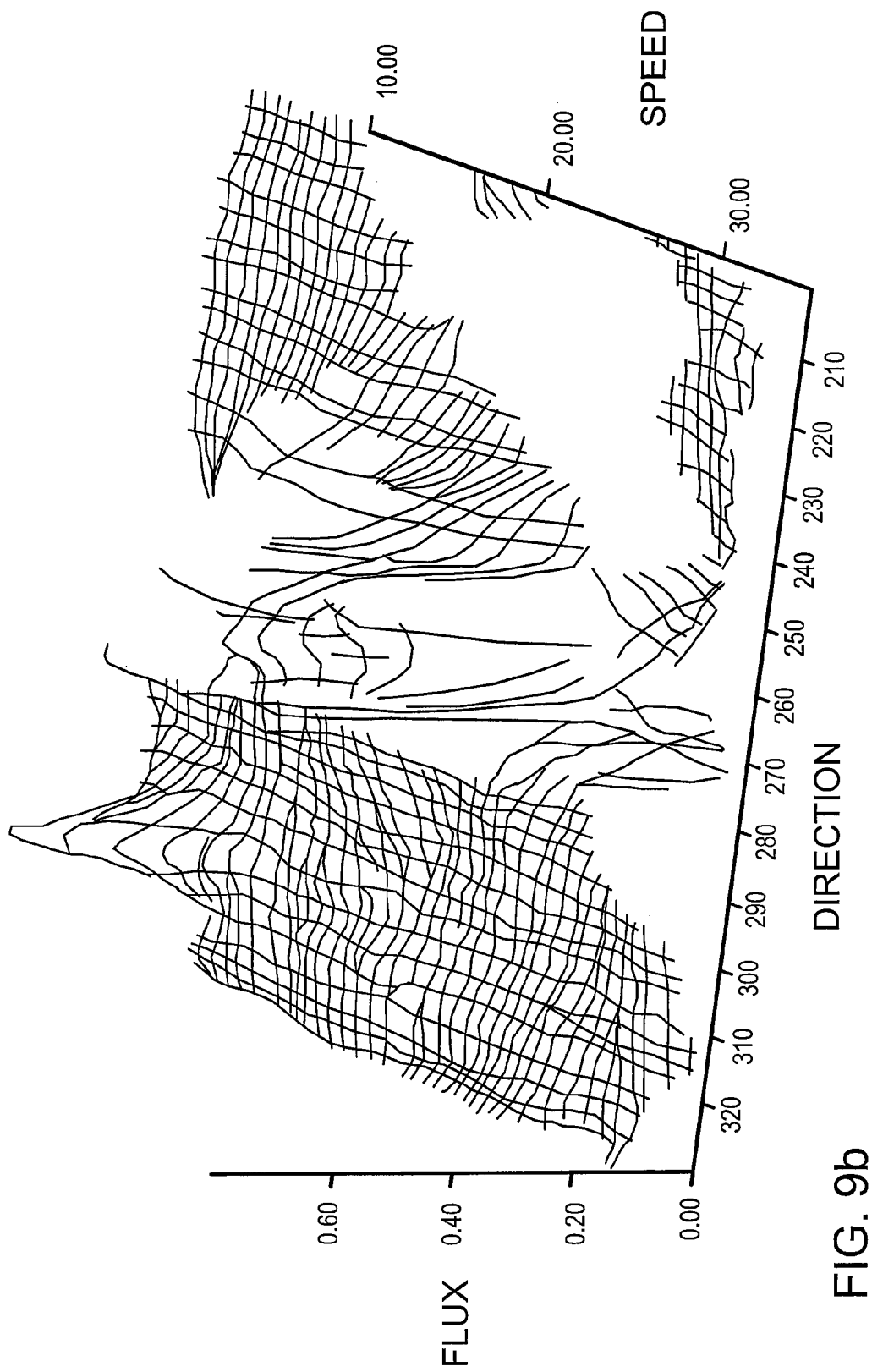
Figure 9C:
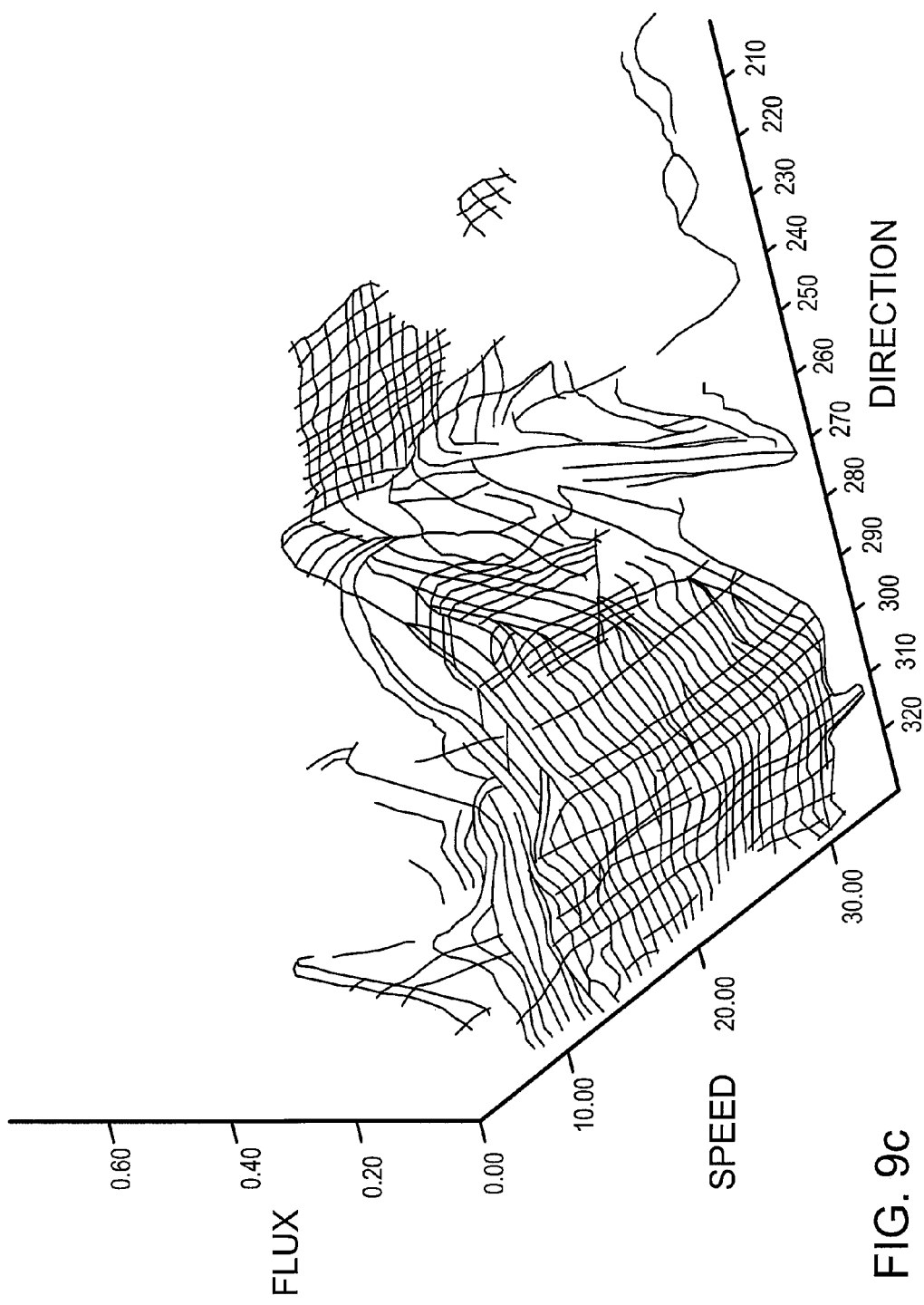
Figure 10:
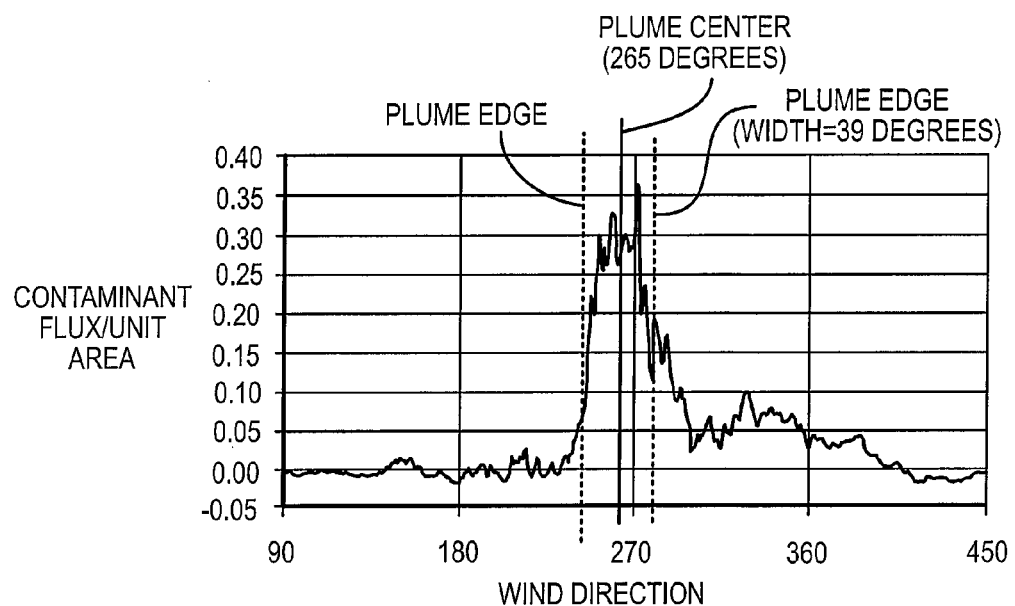

Therefore a corresponding average flux per unit area surface is derived from the average contaminant concentration surface shown in FIG. 8 by multiplying each contaminant concentration value by the corresponding wind speed. FIGS. 8 and 9 illustrate exemplary plume boundaries, trajectories and flux and concentration profiles, and FIGS. 10 and 11 provide a simplified depiction of FIG. 9.

In order to characterize contaminant emitting sources only, the background concentrations of the contaminant monitored are subtracted from the average concentration surface before the flux per area is calculated.

Calculating Vector Plots

This step involves averaging the flux per area table for each increment of wind direction. This will result in one estimate of the flux per area or plume footprint cross-section value for each wind direction and can be plotted as shown in FIG. 10. As shown there are certain wind direction with near zero flux/area values (no sources intercepted (the plume may go over head) in those directions) and other directions with elevated levels (sources in those directions). Typically predominant peaks in the graph correlate with the direction from the sample inlet location to the source of an important emission source. The central line (at 265 degrees) reflects the plume trajectory or direction to the emission source that causes the largest peak. The edges of the peak, marked with dashed lines, generally correspond to the side boundaries or edge of the plume; for example the width of the plume is measured at 39 degrees (this is the dimensionless angular width of the plume).

In accordance with an embodiment of the invention, at least one predominant local peaked flux distribution along the directional component of the wind velocity is identified on the plot of the variation of diluted contaminant flux per unit area. Each local peaked flux distribution is characterized with respect to a peak flux magnitude, a prevailing trajectory or direction and a peak azimuthal width or dimensionless angular width. Dimensionless angular height and other characteristics are also determined, for example, as described in more detail below.

Signal to Noise Rejection analysis may be performed to identify peaks in the flux data from the background or noise.

Characterizing each predominant peaked flux distribution may include fitting the peaked flux distribution to a peaked distribution function. Peaked distribution functions include, but are not limited to: a normal distribution, a Gaussian distribution, a lambda distribution, an exponential distribution, or a step distribution. For example, for a Gaussian distribution the prevailing direction is midpoint of the Gaussian distribution and the azimuthal (angular) width is between one sigma and three sigma out from the midpoint, and the peak magnitude is height of the fitted Gaussian distribution. As another example, for a lambda distribution the prevailing direction is the median, the width is between one sigma and three sigma out from the median, and the peak magnitude is the height of the fitted lambda distribution.

Where fitting is not employed characterizing the predominant peaked distribution includes selecting a pair of flux values to the sides of the predominant peak of the distribution subject to a minimum threshold flux value above the ambient diluted contaminant flux and setting the prevailing direction as the average direction of the pair of flux values.

Alternatively, characterizing the predominant peaked distribution of the directional variation of diluted contaminant flux per unit area includes selecting a pair of directional flux values to the sides of the predominant peak of the distribution of the directional variation of diluted contaminant flux per unit area within a threshold above the ambient diluted contaminant and setting the prevailing direction as the median direction of the flux variation between the pair of flux values.

Allowing for Differences Along Wind Speed and Direction Axes

FIG. 10 is a plot showing average flux variation with wind direction, where flux values at all wind speeds are averaged and plotted against wind direction. Examining the predominant peak that appears in the vector plots in FIG. 10 (between 244 and 285 degrees) with respect to wind speed provides further insight into characteristics of the plume. FIG. 11 shows a plot of the sum of flux/area values between 246 and 285 degrees plotted against wind speed. The graph shows the plume's footprint at the sample inlet 130 at different wind speeds. FIG. 12 shows a pictorial representation of how the position of a plume may be shifted in the vertical direction by the wind for buoyant contaminants and resulting in air samples of different contaminant concentrations being aspired at a stationary sampling inlet 130. The FIG. 11 predicts that the lower edge or boundary of the plume is crosses the sampling inlet 130 at a wind speed of roughly 7 kph and the upper edge or boundary of the plume crosses at a wind speed of 30 kph. The center of the plume crosses at a wind speed of 20 kph. FIG. 11 shows the maximum flux/area value of 0.339 103 m3/yr/m2. These boundaries in terms of wind speed can be converted to a dimensionless angular plume height, for example, as described below. As noted the plume height can be calculated or assumed (also assumed related to the width).

The plume width in FIG. 10 may likely be different at different wind speeds. This is to say that as one moves along the curve in FIG. 11 the plume width may change (typically narrower at higher wind speed, however at very low calm winds may have narrower plumes than some higher wind conditions as the flow may be more laminar).

The average contaminant concentration levels versus wind speed for the wind direction that coincides with a significant source can provide valuable insight into the contribution the emission source has in low wind conditions. This can be useful for compounds where high concentrations will cause problems for example, hazardous contaminants, odor contaminants, or flammable contaminants. Plots of the concentration versus wind speed in the direction of important leaks may be useful. These are produced from column averages between the wind directions of a plume from the adjusted average concentration plots, for example, as depicted in FIG. 8.

Triangulating to Locate Leaks

The directions or trajectories to the important sources identified by predominant peaks in the vector plot(s) FIG. 10 are projected outward from each of the sample inlet locations. Somewhere along the line of each projected vector (prevailing wind direction representative of the peak flux distribution) may be an important emission source. Vectors from the different sampling inlet locations may cross in the vicinity of the contaminant emission source. FIG. 13 shows schematically the prediction of the location of a contaminant emitting source by triangulation from two sample inlet locations. Because multiple vectors are projected from each sample inlet location, some vectors will also cross at locations that are not leaks (ghost leaks). When more than two sample inlet locations are employed confidence in predicting leak locations increases if three or four vectors crossing at a parcel of land. In accordance with an embodiment of the invention, an emission rate of a candidate contaminant emission source corresponding to each sampling inlet location is derived based on the corresponding variation of the diluted contaminant flux per unit plume cross-sectional footprint area, each candidate source being presumed to be located at the parcel of land. Emission rate values of a group of candidate sources are compared. And the location of the contaminant emission source at the parcel of land is asserted based on a substantial agreement between a subgroup of candidate source emission rates of the first group of candidate sources. The subgroup can include the entire group, and the assertion may be made when the number of candidate source emission rates agreeing surpasses a threshold, for example, based on emission characteristics as described above.

A map of the area being monitored may also be correlated with the sample inlet locations. FIG. 14 shows actual results from a facility who's predicted emitting source locations were triangulated from the sample inlet locations. Squares indicate estimated leak locations and circles indicate confirmed leak locations. When a sample inlet location or observation position does not detect plume(s) in a given direction, this is evidence that the corresponding area(s) related to the observation direction or coverage area are free of emission sources.

Quantifying Individual Emission Sources

With the location of an important emitting source predicted above in FIG. 13, an estimate of the emission rate of the corresponding leak is obtained from the data collected from the sample inlet(s) 130. A summary of the individual leak quantification for this leak is shown in the example depicted in FIG. 15 and is described as follows:

the distance from the important leak (1088.8, 136.1) and the remote sample inlet (1193.5, 148.1) is calculated using trigonometry $$\text{distance}=a=((x2-x1)^2+(y2-y1)^2)^{0.5}. a=((1088.8-1193.5)^2+(136.1-148.1)^2)^{0.5}=105.4 \text{ m}$$

the physical width of the plume at the remote sampling inlet is determined by width=$c$=(sin(plume width in degrees from FIG. 10)*$a$ $$c=\sin(39)*105.4 \text{ m}=66.3 \text{ m}$$

area of plume is calculated assuming a circular cross-section area=pi*(width/2)^2)

$$\text{area plume}=\text{pi}*(66.3/2)^2=3452 \text{ m2}$$

the emission rate is flux/area*area of plume where the flux/area value is determined from FIG. 11 (wind speed versus flux/area) and is taken as the maximum value (0.339 103 m3/yr/m2). The maximum value is used because this will be the wind speed were the center of the plume is intercepted by the remote sample inlet and the values plotted in FIG. 11 are basically the integral of the flux/area values across the center of the plume which when multiplied by the plume area will yield the true emission rate.

$$\text{Emission rate}=3452 \text{ m2}*0.339 \text{ 103 m3/yr/m2}=1171 \text{ 103 m3/yr}$$

The Actual location and emission rate of this leak was determined to be (1084.0, 134.5) and 1035 103 m3/yr.

In another embodiment of the technology, the shape of the plume is not considered to be circular. There are many reasons for the shape of the plume not to be circular including non uniform momentum at the point of release, dispersing in noncircular way because of gravity and other dispersion forces, and the plumes may not be circular if the source is an area source (city, tailings pond, etc) or as a result of multiple sources combining.

As described above, the dimensionless angular plume width is projected outward to the correct distance to the source to obtain the scalar dimension of the plume width (horizontal plane). Similarly, the dimensionless angular height of the plume can be projected outward at the correct distance to predict the true scalar dimension of the height of the plume.

A flux versus wind speed plot of a plume, for example, as depicted in FIG. 11, along with the plume vertical velocity (due to buoyancy or momentum) is used to predict the vertical angle of the plume. Combining the vertical plume speed with the wind speed at which the midpoint, leading and trailing edges of the plume are intercepted gives three vectors. The relationship of these vectors can be used to predict the dimensionless angular height of the plume. When projected at the correct distance (i.e. the true distance to the source) this will provide the actual scalar dimensioned height of the plume that will be useful in predicting source characteristics.

It will be appreciated that being able to calculate both the width and height of the plume independently enables the prediction of plume shape and better quantification of sources with non circular plumes. This is also useful for area sources.

It will be appreciated that there can also be some error. For example, the plume size changes with wind speed so when the leading edge is intercepted it will be a larger plume than when the trailing edge is intercepted. The center of the plume is also detectable (FIG. 11 and FIG. 17) as well as the shape of the plume; with some lab confirmation work parameters can be developed to predict the vertical profile of the plume. For example, it may be that the angle between the leading edge and the trailing edge of the plume is the most predictive of vertical dimensions of the plume. The shape of the curves in FIGS. 11 and 17 may be predictable which would enable measuring of just a portion of the figure and extrapolating the rest of it in situations when the plume is not completely intercepted.

When plumes impinge on the ground the concentration profiles will be different and not symmetrical. For example, a plume coming off a city will have a trailing edge but not necessarily a leading edge. This technique will be able to characterize and plume regardless of shape and concentration profile. Observation points at different elevations will be helpful in determining vertical concentration profiles as well because this does not require the plume to move in the vertical plane (due to buoyancy or momentum) like using a single observation does The following is an example calculation of the dimensionless angular plume height. From FIG. 11, the mid point, leading, and trailing edge of the plume is intercepted at wind speeds of 20, 7, and 30 kph (5.6, 1.9, and 8.3 m/s). The plume source and the observation point were located 105 m apart horizontal distance and 27.7 m apart vertical distance. The vertical plume velocity is 1.53 m/s (from source elevation calculation). The angles of the mid point, leading, and trailing edge of the plume are (arc tan(vertical velocity/horizontal wind speed) 15.4, 38.2, and 10.4 degrees. The leading edge minus the trailing edge gives 27.8 degrees height of the plume (note the dimensionless angular width of the plume was calculated at 39 degrees). The leading edge to midpoint is 22.8 degrees while the midpoint to the trailing edge is 5.0 degrees. The plume width is likely changing with wind speed so obtaining the correct angular dimensionless height may require a weighting based on the shape of the flux versus wind speed curve. With controlled studies knowing the vertical dimension of the plume one could develop the appropriate weighting based on the capability according to an embodiment to detect the leading edge, trailing edge, midpoint and pattern of the flux distribution across the vertical plume cross-section to predict the vertical dimensionless angular value.

According to another aspect, quantifying the emission source without assuming a circular cross-section then becomes calculating the plume area using the formula for an ellipse (area=pi*height/2*width/2). Previously the plume width was calculated to be 66.3 m. The plume height is calculated using the dimensionless angular height of 27.8 degrees projected at 105.4 m (distance from observation to source).

Plume height=sin(27.8)*105.4=49.1 m.

It follows that the plume area is:

Plume area=pi*66.3/2*49.1/2=2559 m$^2$

It follows that the emission rate is then calculated as:

Emission rate=2559 m2*0.339 103 m3/yr/m2=868 103 m3/yr

The emission rate calculated here is lower than the one calculated assuming a circular plume (1171 103 m3/yr) and lower than that measured in the field with a bag a stop watch (a one point in time measure). The accuracy of these readings is difficult to determine at this time however, this technique of measuring the plume height has the advantage of not assuming plume shape which may be a big source of error. This technique also provides the added capability of determining the concentration profile across the plume height which gives complete flexibility to quantifying plumes of any shape and concentration profile.

It will be appreciated that an elliptical shape was assumed for the plume because it was coming from a point source. To quantify area sources, a rectangular shaped plume can be used and applying the height and width leads to a better estimate of the emission rate. With these different shaped plumes the average flux per unit cross-sectional footprint area will only be the maximum (as in FIG. 11) if the concentration profile is symmetrical to the centroid of the plume, if it is not then a weighted average is required reflecting the concentration profile.

Good quantification is also possible if the entire width of the plume shifts over a stationary sampling inlet 130 (or if a mobile sample inlet 130/equipment package 110 crosses the entire width of the plume). The profile of the flux/area versus wind speed plot (FIG. 11) may provide a good indication if the entire plume width/extent. If the plot in FIG. 11 shows a distribution that rises and plateaus for a while then decreases again then this may be an indication that the plume shifted its entire width over the sample inlet location. If the flux/area levels do not reach a plateau and then come down (i.e. just rise continually) then this may be an indication only a part of the plume shifted over the sample inlet location. Quantification is possible with only a partially intercepted plume but it may require assumptions of plume shape and concentration profile.

An estimate of the emission rate may be obtained as seen from each sample inlet location. In accordance with one implementation according to an embodiment of the invention, the largest emission rate quantified form all sample inlet locations may be considered as the most accurate assuming that the plume was intercepted best from that sample inlet location. In accordance with another implementation according to an embodiment of the invention, the average emission rate is considered the best estimate.

It may happen, depending on the height of a contaminant plume and the height of a sample inlet 130 that buoyancy would prevent collection of concentration measurements across and beyond the entire plume cross-sectional footprint, to some extent this may be affected by the limited wind speed conditions encountered during the time the concentration measurements were gathered. Whether the entire plume footprint was sampled at a sampling inlet, is determined from the flux surfaces FIG. 9 concurrently with the fitting (Gaussian or lambda) of the flux surface with respect to both wind speed and direction described herein above. The degree R of fit may be employed as a basis for asserting the degree of plume interception. Otherwise, the degree R of fit may be employed to assert whether the sample inlet is below or above the plume.

The assumption that the cross-section of the plume is circular may not always be valid. For example, a non-point source (i.e. source having a shaped opening like a mushroom cap on a tank vent or a large area source like a city on tailings pond) may not have a circular plume cross-section however this assumption may improve with increasing separation distance. A ground level emission source may have a plume that is not circular in cross-section due to the ground effects on the wind distribution (wind decreases closer to the ground). This may distort the lower part of the plume and distort the overall plume shape.

In accordance with an embodiment of the invention, the location of a contaminant source is determined by intersecting vectors passing through the sample inlet locations in the corresponding prevailing directions, computing emission rates for candidate contaminant emission sources located at the intersection and asserting the existence of an contaminant emission based on a substantial agreement between candidate contaminant emission source emission rates. For this purpose, if more than two sample inlet locations are employed, then the substantial agreement is asserted between a group of two candidate contaminant emission sources. For a larger number of sample inlet locations, the substantial agreement is asserted for a subgroup of candidate contamination emission sources defined for example via a threshold number of candidate contaminant emission sources.

Multiple plumes (with all the characteristics plumes shape, concentration profile, variation over time, trajectory both horizontal and vertical) observed from multiple positions are projected out along the trajectory and grouped to determine agreement. All or some of the possible combination of plumes can be checked for predicted source agreement. This can be a large number of combinations, for example if there are eight observation positions that each observe 15 plumes the number of combinations of two or more is 8 choose 15 which is a very large number of calculation that will increase exponentially with increased number of observation positions. The number of plume combinations can become unmanageable if too many observation points are used with too many plumes observed. The number of combinations can be reduced by recognizing not all combinations are valid (i.e. some plume trajectories do not converge so they don't need to be considered) as well there may be the chance to do batches of plumes based on predominance or shape or variability. Each combination of plumes is scored for agreement in the source characteristics considered.

For example, the estimate of horizontal source position can be predicted by averaging the northings and eastings of all the instances of two trajectories crossing and this location can be scored for agreement by summing or summing squares of the perpendicular distance between this estimated position and all the trajectories in the group.

Similarly, a score of the agreement in elevation estimates can be obtained.

Based on the estimated position, the size of the source can be estimated by averaging the size calculated for each observed plume in the group. A score can be calculated relating the agreement in the size estimates from each observation position.

A score of the size agreement can be obtained by summing the difference or the square of the difference of each estimate size from the average.

The agreement in source variability can be scored to see if there is agreement that the source is intermittent (percent of time it is present from each observation position) or the variability in a constant leak. A score of the agreement in plume concentration profile can also be obtained.

By calculating estimated sources from all the combinations of two or more vectors projected out from the observation position and scoring them for agreement in the characteristic categories and then ranking scores (this ranking may be weighted toward one characteristic or another) there will be confidence in asserting the presents of sources at the highest ranked candidate sources. FIG. 19 shows a map generated in this way and based on eight observation positions, denoted by diamond shaped references indicated by 1901, 1902, 1903, 1904, 1905, 1906, 1907, 1908. As shown in FIG. 19, there are groupings of a small number of highly ranked sources (indicated by references 1910, 1912, 1913, 1914, 1915, 1916, 1917, 1918 and 1919) that is likely one source. An estimate of the true source location can be made with help of knowing if there are potentially emitting components in the area in the mapped area, for example as represented by the circles referenced by 1920, 1922, 1924, 1926 in FIG. 19.

Once predominant sources are located with a high degree of confidence then the plumes from these sources can be removed at all the observation points and the analysis run again (i.e. in an iterative way). In this way the dominating effect of the largest sources and the associated plumes can be reduced and smaller more subtle sources and characteristics are better characterized.

Mapping Using Intersections

If multiple contaminant emission sources are present, fact which is ascertained by the number of predominant flux peaks in the flux plots FIG. 9, then unique combination groups of prevailing vectors are defined to include a prevailing vector from each sampling inlets 130, and sub-groups thereof corresponding to individual peaked flux distributions at each sample inlet location are used to ascertain the existence of a source at the locus of intersections of the sub-group of vectors.

Mapping Using Standard Arc Increments

Another way potential source locations may be mapped by includes calculating an emission rate for each location about the locus of sample inlets 130 using the flux values calculated from the vector plots above. The area is broken down into small parcels. Systematically one traverses through the parcels and at each parcel the following is done:

the direction and distance from the parcel to each sample inlet location is determined using trigonometry;

using the vector plot of each sample inlet location, the flux/area values associated with the direction from the remote sampling location to the parcel of land is determined.

an incremental source size is calculated which is the size of a source it would take if this parcel of land contained the emission source that was causing the flux/area values measured and represented in the vector plots for a small standard segment (i.e. one degree) of such a plume. This is done by calculating a plume area associated with this standard segment (equal to sin(standard segment)*distance to remote monitor*assumed plume height) and multiplying by the flux/area value from the vector plot. This is done for each sample inlet location and will result in an incremental source size corresponding to each remote monitoring site.

the incremental source size estimates from each sample inlet location is used to ascertain whether the subject parcel of land is the location of an emission source. This is done by analyzing the distribution of the estimates, if all the incremental source size estimates are tightly grouped around a common value (i.e. small standard deviation) then there would be a high confidence that this is the location of an emission source. The estimate of the size is the average of the incremental source size estimates. Degrees of confidence in weather this is a leak location is determined by how many of the incremental size estimates from the possible total number of sample inlet locations are in agreement.

Accordingly an estimate of the confidence weather it is a leak location and the incremental size of the leak may be obtained. On a map the parcels identified as likely a leak location may be clustered together around an actual leak location. An estimate of the total size of the leak is obtained by summing all the incremental source sizes in the clustered parcels. The estimate of the actual location is the centroid of the clustered parcels.

Each parcel of land can be assigned an estimated leak size and a confidence. The mapping program draws the map of leak locations by both filtering out leaks below a certain size and confidence level.

On a plot of land far away from the source the estimates would have a small standard deviation also, close to zero. For such cases only the direction to a contaminant source is ascertained.

Mapping Using Plume Width Increments

The vector plots in FIG. 10 are employed to predict the size of a plume from an emitting source by using the width (azimuthal width) in degrees across the peak in the vector diagram. These plume widths in degrees can be combined with the distance from the remote sample inlet to the parcel of land to establish the physical width of the plume at the monitor site Plume width=(sin(width in degrees)*distance).

Plume height=(sin(height in degrees)*distance)(if height and width not assumed the same).

Assuming the height and width of the plume are the same (the circular plume cross-sectional footprint assumption), the area of the plume equals $pi*(width/2)^2$ and the average flux across the area determined and combined to provide an emission rate. This will be an estimate of the emission of the source that caused the plume identified. Multiple estimates of an emission rate of a contaminant source enable an accurate and detailed mapping of candidate emission sources.

According to an embodiment, the mapping takes information from the dimensionless angular plume profiles (derived from the Flux versus wind velocity plots) of the observation positions that are relevant to the area being mapped. A plume or a subset of a plume can be projected out along the trajectory for mapping purposes. Individual readings with zero angular width can be projected back along the trajectory as well but a dispersion rate or angular width would have to be assumed in order to adjust the information depending on the distance projected.

The following are possible reasons why the entire plume may not be projected:
 when plume boundaries are not identified because there is not enough data
 when plume boundaries are not defined because there are many plumes blending together
 when plume boundaries are not defined because there is a large area source causing the plume.

Mapping can be done by projecting out along the trajectories of individual readings or groups of readings (grouped based on observation position and meteorological conditions) and correcting the plume information based on the distance projected. Projections from single or multiple observation positions will converge in agreement at the location or area of the true source. These projections can provide the bases to assert the mapped locations, profiles and characteristics of point sources, area sources, or multiple point sources.

When the dimensionless profiles show the absence of plumes this can also be used as valuable information for mapping. Projecting out the absence of plumes can be an indication that the mapped area in question is free of sources. It must be kept in mind that there is a chance a source exists but the observation point missed the plume because it was at the wrong elevation or the source is intermittent and was not emitting when the meteorological conditions were present that would move the plume to the observation point.

Calculating Overall Emissions Rate

The overall emission rate is calculated by adding the sizes of the important individual leaks to an estimate of the smaller leaks that blend into the background. Quantifying the larger leaks was discussed earlier. The plumes from numerous small leaks at facilities can blend together and may not be individually identifiable on the vector plot in FIG. 10. The emissions rate of these emission sources is estimated by: (average flux/area value)*sin(degrees width of the vector plot)*assumed distance to the cluster*assumed plume height. The assumed plume height is a function of the distance to the emission sources. The assumed distance to the cluster of sources is estimated from a map. Alternatively in some situations the location of the remote sampling inlets allows for a rough triangulation to estimate the rough location of the cluster of emission sources which can be to predict the distance between the cluster and the remote sample inlet.

Characterizing the Variability in an Individual Sources Emission Rate (Stability, Frequency, Magnitude of Swings)

Figure 18A:
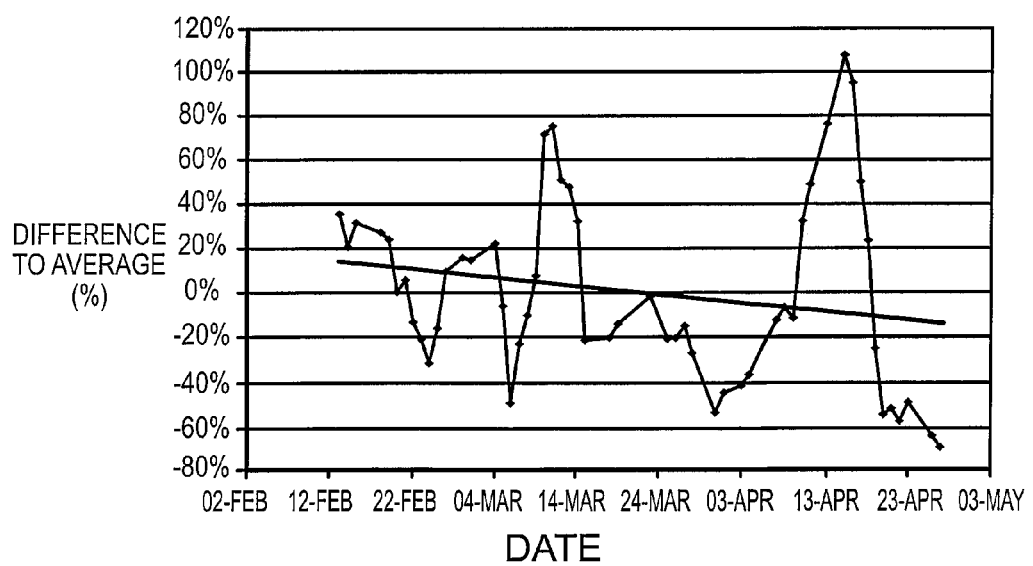

The characteristics of an individual emission source can be characterized over time by analyzing the concentration measure that was taken from within the emission plume boundary. The concentration measurements taken within the plume boundary of a particular source are identified by ranges of wind direction and wind speed at remote sampling locations. The ranges of wind direction associated with a leak are determined in the vector plot of FIG. 10 by the boundaries of the peaks (246 to 285 degrees). The wind conditions associated with a particular leak are determined by the areas of the flux/area plotted vs. wind speed in FIG. 11 and are the wind speeds associated with level well above zero (7 to 29 kph). A better characterization of the variability may be obtained if just the plateau part of the curve is included in the analysis (15 to 25 kph). One can select the concentration measures from the registry of a remote sampling location for the wind speed and direction condition associated with a particular leak and analyze then over time to check for variation in the leakage rate. These measures are stored in the bins with the time stamp of when they were taken. The concentration measure may be multiplied by the wind speed of the compartment were they were stored to obtain a flux/area valve that is analyzed over time as well and may give a more sensitive estimate of the leak characteristics. FIG. 18a shows a scatter plot of the daily average of concentration measure of $H_2S$ versus time corresponding to a remote sampling location. There is not a data point for all the days as the wind did not always blow in the appropriate direction for the remote sample point to pick up the leak. The data has a lot of scatter and shows variability over time with the emission rate finishing much below the average. The data corresponds to an actual leak that was repaired around April 20.

The average of the concentration in these plots is associated with leak quantification done on this leak, the amount that running average varies away from the overall average is considered indication of variability of the leak over time. This variability can be calculated as a percentage ((running average−average)/average) and plotted. Each remote monitoring site can produce a similar plot for the same leak and compared to provide a powerful tool to examine the variability of the leaks overtime. As the multiple remote monitoring sites agree on the trends in the variability, strong conclusions can be drawn on leak variability.

Figure 18B:
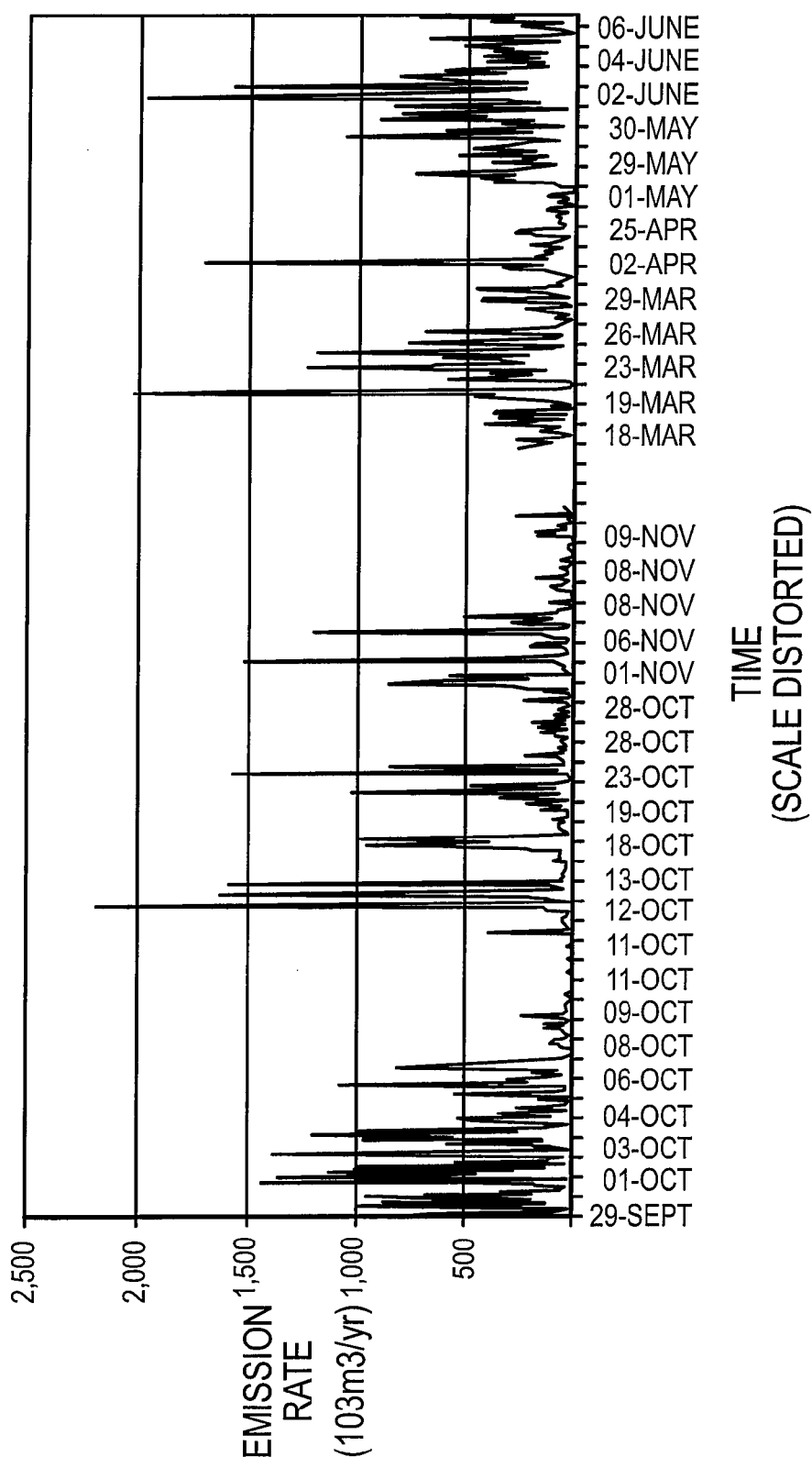
Figure 18C:
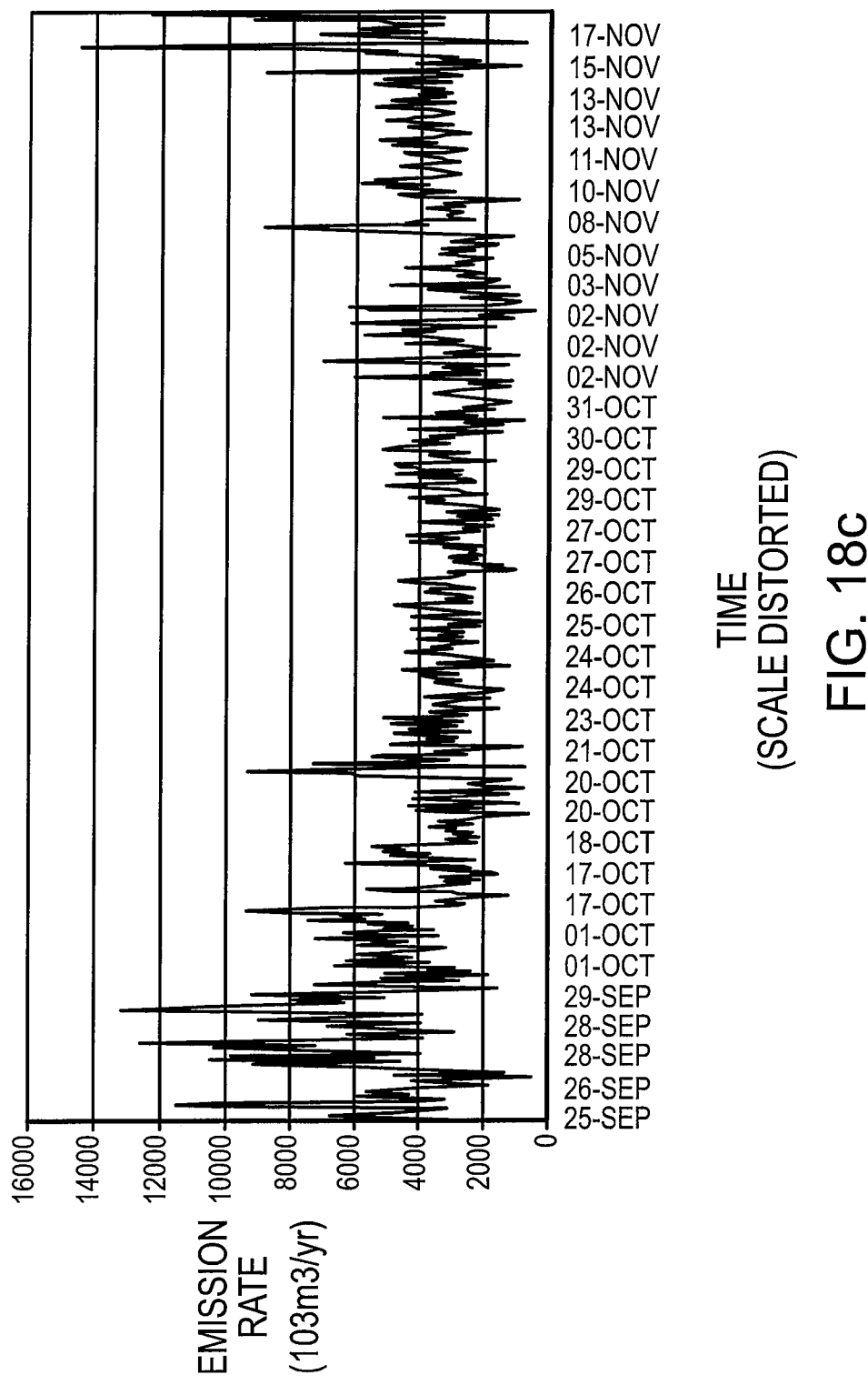

The variation can be plotted in units of leakage rate as shown in FIG. 18b which shows the variability of an emission source (venting condensate tank) over time and FIG. 18c which shows the variability in a large emission source over time. The variations are tracked according to a time scale. By using an exaggerated or distorted time scale the times the plume is not intersected by one of the sample inlets are removed. FIG. 18d is the same data plotted in FIG. 18c except that the time scale is not distorted. FIG. 18d shows that there are periods of time when none of the eight observation positions used in collecting data intercepted the plume.

This technique characterizes intermittent leaks or venting. These measurements of concentration associated with a particular leak are analyzed to look for repeatable patterns that occur on a daily, weekly, monthly or annual cycle. If this was to be done on a daily cycle then the measures would be converted to percentage difference from the average. A running average of the percentage difference form the average is plotted and inspected for variations within the day. Similar plots from each remote sampling site are prepared and compared for consistency in predicting daily trends or anomalies. A similar approach may be taken for any repeated time cycle (i.e. weekly, monthly, annually). Monitoring emission variability is possible at any time cycle and could for example compare the emission rates to different crew shifts.

Quasi Real-Time Surveillance

Near real time surveillance for the occurrence of new significant leaks is possible by analyzing new data (or blocks of new data) soon after collection, and comparing the concentration measurements to those already in the bins of a remote sampling inlet. A process checks if the new data is significantly (this significant level is a parameter that can be set) different than the previously acquired data. If the differences exceed a certain limit, then a flag is raised to warn that an unexpected leak has changed, or perhaps a new leak has appeared. Operators may have the option to waive the warning and add the data to the bins or to keep the measurements separate while more measurements are collected, when the new measurements could be discarded (if the anomaly in the facility was identified and fixed) or added to the bins if it is a change in operation that will continue. The new data is compared to any historical time period by setting a parameter. This time period is implemented as a rolling window that moves forward.

Real Time Monitoring

According to this embodiment, surveillance is provided to determine a changing emission source in real time or near real time. According to this embodiment, the data streaming from a detector is tracked in near real time and compared to the readings of what is to be expected and taking specific action if unexpected readings are received. What is expected can be based on the pattern of emissions at an observation location developed from historical measurements or assumed, for example, one could assume no emission sources or expected patterns based on known emission sources. When readings are not what we expected, then we one or more of the following actions can be taken:

1. do nothing different
2. check if the reading is real or an artifact by
   a. checking equipment function
   b. is there repeated evidence of a deviation from this observation point
   c. is there confirmation of the deviation from other observation positions
   d. check if there is any record of similar deviation logged with similar circumstances
3. log the deviation for future reference
4. sound an alarm
5. refine the mapping of the new source by reanalyzing the data with more accurate assumptions (i.e. distance to source)
6. changing where samples are being taken from to have the best chance at intercepting the plume of the new or changing source. This is refocusing the data collection to "chase" the new or changing emission source
7. subtracting the variant signal from the background at all sample inlets and mapping the differences from the background Where an area has been under surveillance for some time there may be a substantial data history that will enable statistical power in asserting whether a reading is out of the ordinary or not. If there is not historical measures to compare readings to then the thresholds to take different action at can be assumed.

This near real time surveillance may be applied to mobile detectors. If an area has been traversed by mobile detectors before then there may be a history able to compare new readings to that are geographically and meteorologically specific. If a lot of data has been collected over certain paths or an area, then the statistical power to predict new or changing emission patterns increases. If it is the first time an area has been traversed by mobile monitors then one may not be able to be as sensitive to new or changing emission sources and one will have to rely on thresholds for asserting the presents of sources based on assumed values derived from experience.

Focused Monitoring

Focused monitoring refers to the technique of changing which remote sampling sites are analyzed based on an analysis of wind conditions. Under normal conditions the valves that control which remote sample location gets analyzed are on a predetermined cycle that steps through every valve in sequence and hold for a predetermined length of time at each valve (i.e. three minutes at each valve position). Under focused monitoring the valve sequencing is adjusted to reflect expected or measured wind conditions. This technique is useful if information on fugitive emissions is desired from a particular location in a facility. If the predominant wind is from the west then the valve sequencing is predetermined to pause for longer time periods at the eastern remote sampling locations if the focus of the analysis is on the facility. The valve sequencing can be adjusted on the fly as well to accommodate changes in the wind direction by adopting predetermined sequencing patterns for different conditions of wind direction and speed. Lastly the valve sequence can be adjusted to focus the surveillance at new areas that arise from the results that emerge from the quasi real time surveillance. If the quasi real time surveillance identifies something different occurring in the air concentration measurements and the triangulation algorithms establish the area of the anomalous emissions then the focused monitoring algorithms adjust the valving sequences based on the current wind direction to provide surveillance to the emerging area of concern, for example, chasing down a new leak).

According to another embodiment, the data collection or observation position locations can be adjusted to "chase" the emitting source. In general it involves moving the observation point to better intercept the plumes from sources.

According to another aspect, the raw data can be re-analyzed with new assumptions to refocus the analysis and get a clearer more accurate picture in a adjusted location. Initially analysis requires assuming a distance to the source once a good idea of source locations are obtained, the raw data is re-analyzed with better assumptions of the distances from each observation position to the sources and more accurate characterization of the sources can be achieved.

Longer Time Needed to Characterize Intermittent Leaks

Continuous leaks will provide a constant signal that may allow for the characterization of sources when the wind blows in the appropriate directions. The length of time needed to adequately characterize an area for emission sources is dependent on the frequency of the wind blowing from the appropriate direction and the frequency of the cycling of the remote sampling array. Focused monitoring can shorten the time needed by adjusting the frequency of the remote sampling array to match the frequency of wind blowing the right way. With intermittent sources there is the frequency of the emission source to overlay on top of the frequency of the remote sampling array and the frequency of the wind blowing the right way.

In summary, to obtain concentration measurements on a contaminant source the wind must be blowing in the right direction, the remote sampling inlet must be active, and the source has to be emitting all at the same time. If these three requirements are satisfied only infrequently, then it can take a long time to gather enough data to characterize the emission source. Adjustments can be made to try and decrease the time needed by moving the location of the remote sampling inlet or adjusting the frequency of the remote sampling array through focused monitoring. In general intermittent sources that emit infrequently will take longer to characterize.

Mapping and Stating the Confidence of the Predictions

Early (timely) contaminant source predictions may be valuable even if they have higher margins of error than later confident contaminant source predictions. The confidence in predictions made may be included in output to help with the interpretation of the results. This allows for the release of early results with warnings of margins of error that will be different in the different areas of the map depending on the wind directions that have occurred. Predictions based on numerous measurements may be very accurate while prediction based on few measurements will have higher margins of error but still may be valuable if delivered in a timely manner.

Predicting Elevations of Emission Sources

The pattern of the flux/area values in FIG. 11 will be different depending on the elevation of the remote sample inlet, the elevation of the source, and the rising nature of the plume due to buoyancy or momentum (up or down). The following describes how the elevation can be predicted (for example, see FIG. 16):

the vertical velocity (Vy) of the plume is estimated as:

$$Vy=c/(a*(1/Vx1-1/Vx2))$$

where Vx1 and Vx2 are different wind speeds when the plume center intercepts the remote sample inlets r1 and r2.

then the height of a fugitive source (b) is determined $$b=r2h-(Vy*a/Vx2)=r1h-(Vy*a/Vx1)$$

where $r2h$ and $r1h$ are the height of the remote sampling inlets and a1 and a2 is the distances from the emission source to the remote sample inlets (in this example in the remote sample inlets are at the same location, a1=a2).

A single monitor is able to use the two different wind speeds that the monitor intercepts the top and bottom edge of the plume to estimate the source height by knowing the physical size of the plume (height=width from quantifying section=(sin(39)*a). This method may also be used to estimate plume dimension if Vy is known. According to another embodiment, non-linear vertical trajectories of the plumes due to weather inversions, plume buoyancy, land topography, or obstacles like buildings, and the like, are considered.

FIG. 17 shows two flux/area versus wind speed plots taken from two remote sampling inlets at the same location but at different elevations (13.7 m and 18.3 m). The following is a sample calculation of the elevation of the emitting source:

$$Vy=c/(a*(1/Vx1-1/Vx2))$$

$$c=(18.3-13.7)=4.6 \text{ m}$$

$$Vx2=21 \text{ kph}=5.83 \text{ m/s}$$

$$Vx1=18 \text{ kph}=5.0 \text{ m/s}$$

$$a=105.4 \text{ m (from previous)}$$

$$Vy=1.53 \text{ m/s}$$

$$b=r2h-(Vy*a/Vx2)$$

$$r2h=13.7 \text{ m}$$

$$b=-14.0 \text{ m (the remote sample location was at higher evaluation)}$$

The apparatus and methods presented herein may be employed to locate and quantify any source of airborne emissions as long as the emission contains a compound or particulate which can be detected with an analyzer at levels distinguishable above background concentrations thereof.

Reference is next made to FIGS. 20 to 23 which show in flowchart form processes or methods according to embodiments of the present invention.

Reference is made to FIG. 20 which provides an overview process flow of processes according to an embodiment of the invention. The processes as depicted in FIG. 20 comprise a monitoring/tracking process 2010, a mapping process 2020, and a data acquisition or surveillance process 2030.

The data acquisition/surveillance process 2030 is concerned with the collection of contaminant concentration and meteorological-related and land-use data according to an embodiment. The collected data is stored in a database or a datastore/archive indicated generally by reference 2040 in FIGS. 20 and 21. According to an embodiment, the process 2030 can collect or manipulate data based on input from the mapping process 2020 and/or the monitoring/tracking process 2010, as depicted in FIG. 20. According to an embodiment, the monitoring/tracking process 2010 checks data from the data acquisition process 2030 against baseline data to determine changes in emission sources and/or emission levels in the area being monitored. According to an embodiment, the monitoring/tracking process 2010 is implemented to modify or refocus the operation of the data acquisition process 2030 and/or the mapping process 2020 in response to one or more monitored events. According to an embodiment, the mapping process 2020 generates one or more maps that identify the location(s) of emission sources based on data collected by the data acquisition process 2030. The mapping process 2020 may also utilize data retrieved from the datastore 2040. According to another aspect, the mapping process 2020 is implemented to refocus or alter the map based on input from the system user, the monitoring process 2010 and/or previously generated maps. According to another aspect, the map(s) generated according to the mapping process 2020 are utilized to target surveillance and/or monitoring/tracking.

Reference is next made to FIG. 21, which shows an embodiment of the data acquisition or surveillance process 2030 in more detail. According to one aspect, the data acquisition process 2030 is implemented with "where" and "when" parameters for performing surveillance, i.e. data acquisition. The "where" parameter defines the area or space under surveillance and has virtually no limits, for example, data can be acquired for a large area, e.g. a province or country, or for a small area, e.g. an industrial facility, building or compound, or both with a maps showing larger areas with focus on small or sub areas. The "when" parameter defines the time frame of the surveillance or data acquisition, and can go back in time based on previously captured or archived air quantity data and meteorological data is available. According to another aspect, the "when" parameter can be defined for near or real time data acquisition.

According to an embodiment, the data acquisition process 2030 relies on user input 2110 to define the parameters for time and space as indicated by reference 2112 in FIG. 21. According to another aspect, the process allows the user to interact with the surveillance or data acquisition by changing the original objectives, for example, to better characterize an identified or potential emission source, as indicated by 2120. For example, the user can identify an area and time to focus the surveillance or indicate an area for special monitoring. According to another aspect, the process triggers the mapping process 2020 (FIG. 20 and FIG. 22) to update the map. As also shown in FIG. 21, the data acquisition process 2030 includes the capability to gather information or data on land use, topography, buildings, obstructions, known sources, potential sources, as indicated by reference 2122. For example, available information is gathered on land use and topography or obstructions that may affect the movement of the air. Knowledge of these obstructions and there geometry can be used when projecting the plume back along its trajectory to make adjustments for the obstructions. Knowledge of known sources and potential sources can be used in the mapping algorithms to better estimated source characteristics.

According to another aspect, the data acquisition process 2030 is configured to collect relevant data existing for example in historical archives, as indicated by 2130. The historical or archived data can include contaminant concentrations (air quality) and meteorological conditions (i.e. wind velocity) relevant to the space and time in question from any available source. The data can also include the observation positions of the readings that generated the data (for example, readings could be from mobile monitors). This data is put into the datastore 2040 and is made available for the processes as described above. According to another aspect, the utilization of historical datasets in accordance with the methodology according to the present invention provides the capability of mapping and characterizing emission sources back through time based on data from air monitoring networks that have been in operation.

As shown in FIG. 21, the data acquisition process 2030 includes a module for the collection new data, e.g. locations, frequency, stationary or mobile, as indicated by reference 2140. According to an embodiment, the process module 2140 determines the strategy for collecting new data based on the air monitoring equipment available and the space/time parameters set for surveillance. For example, the monitoring equipment may be installed in permanent location(s), part of a cycled inlet array, stationary but movable, and mobile monitoring. Refocusing of the surveillance on smaller locations or other locations based on user initiated changes or the emergence of new or changing sources can results in changes to the deployment of the monitoring equipment or changes to the sample inlet locations to better track the new areas or the new sources.

As shown in FIG. 21, the data acquisition process 2030 includes a module 2150 for taking measurements of emissions, e.g. contaminant concentration measurements. The module 2150 utilizes detectors for example as described above, and in general, any detector of the target compound can be used (including open path detectors which would be a line or plane of observation rather than a point of observation for traditional detectors). According to an embodiment, the detectors are connected to a manifold and are cycled through multiple remote sample inlets that would enable multiple observation positions from one detector. The monitoring equipment may be installed in permanent locations, part of a cycled inlet array, stationary but movable, and mobile monitoring.

As shown in FIG. 21, the data acquisition process 2030 includes a module 2160 for gathering or making meteorological measurements. As described, wind velocity is used to determine emission sources according to an embodiment. In addition to wind velocity, other data suitable for predicting air movement or vertical mixing characteristics of the atmosphere (e.g. temperature inversions) including but not limited to vertical wind speed, sun light intensity, temperature, and humidity can be gathered or measured. According to another aspect, any relevant public meteorological data can be collected and/or with the deployment of other meteorological equipment used to fill in any gaps. The meteorological conditions for the time and space the plumes are being traced through will be based on interpolations and extrapolations of the meteorological data available taking into account the effects of topography or obstructions on air movement.

As shown in FIG. 21, data captured or collected by the data acquisition process is stored in the datastore 2040. According to an embodiment the datastore 2040 holds the relevant time stamped information and makes it available to the mapping process 2010 and the quasi real-time surveillance algorithm. Determining relevant information is based on the objectives and what is available.

Reference is next made to FIG. 22, which shows in more detail an embodiment of the mapping process 2020. As shown, the mapping process 2020 includes a process module 2210 for generated or updating a more detailed or focused map. According to an embodiment, the process module 2210 is triggered or invoke by a preset time-out or interval, a user input or a trigger from a real-time monitoring operation. In response, a process is initiated to update the emissions map. A focused map is achieved by mapping sources with good assumptions of the distance from the source to the observation positions. Areas of maps may have different distance assumptions than other areas depending on the relative positions of the observation potions and the source locations. According to one aspect, a map can comprise a patchwork of smaller sub areas with specific area focus. This patchwork can be achieved by either zeroing in on the important sources through and iterative approach or a brute force approach that breaks the area down into smaller areas and generating a focused map for each smaller area and then combining them into the larger overall map after. The second approach may be better for area sources because depending on the proximity of the observation positions, the area sources may not converge with a zeroing in approach.

According to an embodiment, the mapping process 2020 includes a process module 2220 for determining assumptions that support time and space focus. When the mapping refresh starts the first step is to gather the data from the archive and determine the applicable and current time and space focus from the surveillance and monitoring routines.

According to an embodiment, the mapping process 2020 includes a process module 2230 for calculating dimensionless plume profiles, for example, as described in more detail above. The current profiles are stored for reference. These profiles are calculated by projecting contaminant readings back along the trajectory traveled and analyzing as described previously.

According to an embodiment, the mapping process 2020 includes a process module 2240 for providing surfaces associated with the dimensionless plume profiles. The profiles are passed to the mapping process and are available to the monitoring routine establish the expected values to compare with new reading(s).

According to an embodiment, the mapping process 2020 includes a process module 2250 for generating a map. The process module 2250 takes the inputs and predicts source characteristics including location. As indicated by reference 2260 in FIG. 22, the map comprises individual sources (size, variability, location), area sources (location, area profile, size, variability) and can also include information available on the sources for this area or sub area. According to another aspect, the map shows areas or regions that do not have any emission sources, i.e. are emission source free. It will be appreciated that an observation position that does see any plumes in its direction or quadrant provides an indication that the area is emission source free. As shown in FIG. 22, the mapping process 2020 includes a process module 2270 for comparing sources location and timing with space/time focus (maybe source specific). According to an embodiment, the estimated source information is compared to the assumptions used in the calculation to see if any refocusing is required. Any adjustments needed to the assumptions are communicated with the appropriate process or routine. As shown in FIG. 22, the mapping process 2020 includes a process module 2280 for updating the map or sub-areas of the map. According to an embodiment, the updates are intended to show characteristics of important sources, for example, individual and overall area emissions, or the emergence of new or changing sources. According to an embodiment, the maps of any sub-areas that have been generated in previous runs of the mapping routine are combined (i.e. pieced together) to form the overall map.

Reference is next made to FIG. 23, which shows in flowchart form an embodiment of the monitoring/real-time tracking process 2010. The monitoring process 2010 includes a process module 2310 for tracking or collecting new contaminant readings, observations and/or meteorological conditions. According to an embodiment, the process module 2310 process grabs the new contaminant reading along with where the reading was taken and the relevant meteorological conditions. If there are multiple detectors deployed then there will be multiple sets of data. The process module 2310 passes this information to a process module 2320 which comprises a comparison operation.

According to an embodiment, the process module 2320 determines what contaminant levels are expected at the given observation points under the given metrological conditions. According to one aspect, the process module 2320 determines the expected levels based on assumed background levels and/or assumed action thresholds and/or historical data summarized in the dimensionless plume profiles. Next in decision block 2322, the new readings are compared to the expected levels. The next step depends on whether it is found to be different or not. If there is more than one contaminant detector collecting information then this decision will be made for each information stream. If they are not different then nothing happens and a normal condition is signaled to the user. If the concentration levels are not in line with the expected levels, then a process module 2330 to archive the levels is executed. According to an embodiment, the process module 2330 gathers the readings including any relevant position and meteorological information and sends it to a variant archive 2332 for storage and future reference. The variant archive 2332 stores unexpected readings and relevant associated information (meteorological and observation position). Data can be removed from this archive if it seen as no longer relevant to the issue of new or changing emission sources. This may be after a prescribed time period, if the changing emissions have been resolved, or based on the user electing to ignore the variances. This archive is past to the next step where it is analyzed for every unexpected or group of unexpected readings.

According to an embodiment, the process module 2330 analyzes variant characteristics. According to an aspect, the process module 2330 checks the archive of unexpected readings looking for consistencies that would establish proof of an important emerging or changing emission source. If the information is inconclusive or incomplete, the process provides direction how to collect more or better data or improve the analysis to make better decisions. In general this process decides what action to take by sending indicators to the following decision steps to trigger actions:

1. Sound Alarm Process (2340)—according to an embodiment, an action is triggered where the users are alerted to a new or changing emission source. This process will notify the user of an alarm conditions and indicate best estimate of source characteristics and location on map. This alarm could be on the live map that is updated periodically in the mapping algorithm. This alarm could convey the information available about the new or changing source including size or location on the map (to the best accuracy available at the time. This process communicates with the mapping process 2020 (FIG. 20).
2. Map Deviations Process (2350)—according to an embodiment, a variant archive being sent to the mapping process 2020 (FIGS. 20 and 22) is triggered to generate a map of the unexpected readings with the appropriate time and space assumptions. The mapping could us the variant readings or the difference between the variant reading and what is expected. The second approach would track the difference from the background and will be able to differentiate new or emerging sources over and above any background sources that exist. This action will communicate with the mapping process 2020 (FIGS. 20 and 22).
3. Refocus data collection process (2360)—according to an embodiment, a trigger is generated to adjust how the new data will be collected to better track or "chase" a new or emerging source. It will be based on whether you want to disrupt the existing sampling routine to gather different information that may be more applicable to new or changing sources. The adjustment to the data collection will be made in the surveillance process 2030 (FIGS. 20 and 21). This process may determine how to best make the adjustment and communicate this with the surveillance routine. The adjustment could entail adjusting the sampling positions to better intercept a plume from a suspected emerging or changing source. The sampling position can be adjusted by changing the active sample inlets on an inlet array, move a mobile detector or redeploy a detector or inlet to be in a different position. These adjustment are to support a new time and space focus. This process communicates with the surveillance process 2030 (FIGS. 20 and 21).

4. Refocus data analysis with action process module (2370)—according to an embodiment a trigger is generated to change the space and time focus assumptions used in the mapping algorithm. The decision whether to changing the space and time focus will be based on whether one can improve the focus of the analysis by having a better estimate as to the distance to the sources. This is part of an interactive approach as initial assumptions of the distance and time focus must be made (to meet the overall objectives) and then adjusted as the mapping routine produces estimates of the location and timing of emitting sources. Once more is known about sources better assumptions of the distance and time to sources can be made. Different areas of a map may have different distance to the source assumptions for the different source. These assumptions will continue to be adjusted as more data is collected and the sources become better defined through out the surveillance period. According to an embodiment, the process communicates with the mapping process 2020 (FIGS. 20 and 22).

5. Censor variant data process module (2380)—according to an embodiment a trigger is generated to flag variant readings in the data store so that future analysis may choose to include or exclude it from future analysis. According to an embodiment, this decision is based on how the user wants anomalous conditions to affect the historical data set and future analysis. For example, excluding anomalies results in a cleaner baseline which allows the monitoring algorithm to be more sensitive future anomalies.

While extensive reference has been made to detecting gas leaks at natural gas plants and the like, the invention is not limited thereto, the apparatus and methods described herein may also be used for:

Fugitive emissions at industrial facilities where it can, measure the facility wide emission rate and localize and quantify the important sources Characterizing known emissions sources at industrial facilities (i.e. stack monitoring).

Regional emissions monitoring

Characterizing odors in rural or urban areas

Policing applications like locating and characterizing drug labs, grow-ops

Providing surveillance of buildings (security guards with mobile monitors could characterize a hotel or apartment for explosives or drugs.

Characterizing emissions from a community

Regional surveillance of pipe line leaks

Local surveillance of pipeline leaks

Characterizing emission related to site remediation work

Characterizing emission from storage tanks or tank farms

Characterizing emissions from tailings ponds

Characterizing sources and sinks of compounds in the environment (e.g. Mercury, methane)

Calibrating air dispersion models

Military applications include locating unknown explosives

The previous description of the disclosed embodiments is provided to enable any person skilled in the art to make or use the present invention. Various modifications to those embodiments will be readily apparent to those skilled in the art, and the generic principles defined herein may be applied to other embodiments without departing from the spirit or scope of the invention. Thus, the present invention is not intended to be limited to the embodiments shown herein, but is to be accorded the full scope consistent with the claims, wherein reference to an element in the singular, such as by use of the article "a" or "an" is not intended to mean "one and only one" unless specifically so stated, but rather "one or more". All structural and functional equivalents to the elements of the various embodiments described throughout the disclosure that are known or later come to be known to those of ordinary skill in the art are intended to be encompassed by the elements of the claims. Moreover, nothing disclosed herein is intended to be dedicated to the public regardless of whether such disclosure is explicitly recited in the claims.

The embodiments presented herein are exemplary only, and persons skilled in the art would appreciate that variations to the embodiments may be made without departing from the spirit of the invention. The scope of the invention is solely defined by the appended claims.

What is claimed is:

1. An apparatus for characterizing a source of an emitted material, said apparatus comprising a computing device with peripheral devices and subsidiary units, operatively connected with each other and programmed to perform specific functions, those parts comprising:

a data store to store and retrieve sensor data comprising information about the concentration of the emitted material in a flowing fluid at a particular time and a particular location, the sensor data having been collected from a plurality of locations at one or more times to a data store to store and retrieve information about the velocity of the flowing fluid, being the speed and direction of the flow of the fluid at points in time and space, the information being in respect of a plurality of times and locations, said velocity- information-related times being proximate to the times of the emitted-material-concentration-information and the velocity-information-related locations being relevant to the sensor location of any source in the sense that the fluid containing the measured concentrations of emitted material had been affected by the fluid velocity being saved a dimensionless plume generating unit, for generating a series of dimensionless plumes in space for each sensor location over time using the sensor data and the fluid velocity data as inputs to the dimensionless plume generating unit a trajectory generating unit, for correlating the generated dimensionless plume location series for each sensor location from the dimensionless plume generating unit with fluid velocity information from the data store by reference to time and generating a trajectory for each such generated plumes a modeling unit which uses the plume trajectories from the trajectory generating unit and generated dimensionless plumes from the dimensionless plume generating unit as inputs to a model and projecting a modeled plume back along its trajectory in a calculated direction of its probable source for each dimensionless plume, calculating a predicted candidate location for an emission source location and at least one further emission source characteristic a plume conversion unit, for converting each series of dimensionless plumes for each sensor location to one or more .dimensioned plumes at such location at one or more relevant particular times and using the dimensions of the dimensioned plume at each sensor location at each particular time, determining a plume size characteristic relevant to the emission source location predicted by operation of the modeling unit using the dimensions of the dimensioned plume at each sensor location at each particular time, determining a plume size variability characteristic over time relevant to the emission source location predicted by operation of the modeling unit; and a comparator unit, for matching and comparing the plume size variability characteristics relevant to each emission source location predicted for each sensor location to reduce the list of possible candidate predicted emission source locations to those which most closely match, the comparator unit scoring potential sources' locations based on: horizontal location, size or emission rate, size or emission rate variability, and vertical location.

2. The apparatus as claimed in claim 1, wherein said plume size variability characteristics associated with said emission source candidates include one or more of emission rate variability, horizontal emission location, vertical emission location, emission exit momentum, emission buoyancy, point emission source, area emission source, multiple emission sources, plume concentration profile for emission.

3. The apparatus as claimed in claim 1, wherein the plurality of concentration measurements recorded are made by a sensor stationed at a first location and then a second location.

4. The apparatus as claimed in claim 1, wherein said representative wind velocity information comprises information about the velocity of wind flowing somewhere between the emission source toward the measurement locations during a relevant time.

5. The apparatus as claimed in claim 1, wherein the plume conversion unit determines a size characteristic based on said dimensioned plume by first determining a flux within the dimensioned plume and background flux level, and subtracting the background flux from the flux within said dimensioned plume, and multiplying the flux difference with an area measurement of said dimensioned plume.

6. The apparatus as claimed in claim 2, wherein the plume conversion unit determines a size characteristic by first determining the emission rate variability, and said emission rate variability being determined by comparing one or more concentrations measured within said dimensioned plume to an average concentration measurement and the emission rate variability comprising deviations from the average concentration measurement.

* * * * *